US010240180B2

(12) United States Patent
Northen et al.

(10) Patent No.: US 10,240,180 B2
(45) Date of Patent: Mar. 26, 2019

(54) MULTIPLEXED SCREENING OF ENZYME ACTIVITIES USING NANOSTRUCTURE-INITIATOR MASS SPECTROMETRY

(75) Inventors: Trent R. Northen, Walnut Creek, CA (US); Wolfgang E. Reindl, Berkeley, CA (US); Kai Deng, Albany, CA (US); Seema Singh, Fremont, CA (US); Anup K. Singh, Danville, CA (US); Xiaoliang Cheng, Albany, CA (US)

(73) Assignees: The Regents of the University of California, Oakland, CA (US); National Technology & Engineering Solutions of Sandia, LLC, Livermore, CA (US)

( * ) Notice: Subject to any disclaimer, the term of this patent is extended or adjusted under 35 U.S.C. 154(b) by 0 days.

(21) Appl. No.: 13/363,695

(22) Filed: Feb. 1, 2012

(65) Prior Publication Data
US 2012/0225797 A1    Sep. 6, 2012

Related U.S. Application Data

(60) Provisional application No. 61/438,586, filed on Feb. 1, 2011.

(51) Int. Cl.
| | | |
|---|---|---|
| C40B 30/10 | (2006.01) | |
| C40B 20/04 | (2006.01) | |
| C40B 20/08 | (2006.01) | |
| C12Q 1/00 | (2006.01) | |
| B82Y 30/00 | (2011.01) | |
| C40B 40/04 | (2006.01) | |

(52) U.S. Cl.
CPC .............. *C12Q 1/00* (2013.01); *B82Y 30/00* (2013.01); *G01N 2560/00* (2013.01)

(58) Field of Classification Search
CPC ....................................... C40B 30/08
USPC .................................... 506/7, 11
See application file for complete search history.

(56) References Cited

U.S. PATENT DOCUMENTS

| | | | |
|---|---|---|---|
| 2004/0023274 A1* | 2/2004 | Shinohara | 435/6 |
| 2005/0244891 A1* | 11/2005 | Graham et al. | 435/7.1 |
| 2006/0160167 A1* | 7/2006 | Elased | G01N 33/573 435/23 |
| 2008/0128608 A1 | 6/2008 | Northern et al. | |
| 2012/0225797 A1 | 9/2012 | Northen et al. | |
| 2015/0330992 A1 | 11/2015 | Northen et al. | |

FOREIGN PATENT DOCUMENTS

EP    0973937 B1    4/2006

OTHER PUBLICATIONS

Ranwala, Anil P. et al., "The Role of beta-Galactosidases in the Modification of Cell Wall Components during Muskmelon Fruit Ripening," 1992, Plant Physiology, 100, pp. 1318-1325.*
Mahajan, Sonam and Emma R. Master, "Proteomic characterization of lignocellulose-degrading enzymes secreted by Phanerochaete carnosa grown on spruce and microcrystalline cellulose," Mar. 20, 2010, Appl. Microbiol. Biotechnol., 86, pp. 1903-1914.*
Min, Dal-Hee et al., "A Method for Connecting Solution-Phase Enzyme Activity Assays with Immobilized Format Analysis by Mass Spectrometry," Jul. 15, 2004, Analytical Chemistry, 76, pp. 3923-3929.*
Turecek, F. 2002 Journal of Mass Spectrometry 37: 1-14.*
Haugland, Rosaria P. and Wendy W. You "Coupling of Anitbodies with Biotin." in: Methods in Molecular Biology, vol. 418 Ed. R. J. McMahon (Totowa, NJ, Humana Press, 2009), pp. 693-703.*
Brulc J et al 2009 PNAS 106: 1948-1953.*
Gurard-Levin et al, Combinind Self-Assembled Monolayers and Mass Spectrometry for Applications in Biochips, Annu. Rev. Anal. Chem., 2008, 1, 767-800.*
Kilbanov, A., Improving Enzymes by Using Them in Organic Solvents, Nature, 2001, 409, 241-246.*
Hedstrom, L., Enzyme Specificity and Selectivity, Encylopedia of Life Sciences, 2010, 1-8.*
Horvath, A., Solubility of Structurally Complicated Materials: I. Wood, J. Phys. Chem. Ref. Data, 2006, 35(1), 77-92.*
Wallengstein et al., Controls on the Temperature Sensitivty of Soil Enzymes: A Key Driver of in Situ Enzyme Activity Rates, Chapter 13, Soil Enzymology, 2011, 245-258.*
Woo et al., Nanostructure-Initiator Mass Spectrometry: A Protocol for Preparing and Applying NIMS Surfaces for High-Sensitivity Mass Analysis, Nature Protocols, 2008, 3(8), 1341-1349.*
Patti et al., Detection of Carbohydrates and Steroids by Cation-Enhanced Nanostructure-Initiator Mass Spectrometry (NIMS) for Biofluid Analysis and Tissue Imaging, Analytical Chemistry, 2010, 82(1), 121-128.*
Greving et al., Nanostructure-Initiator Mass Spectrometry Metabolite Analysis and Imaging, Analytical Chemistry, epub 2010, 83, 2-7. (Year: 2010).*
Allgaier et al., Targeted Discovery of Glycoside Hydrolases from a Switchgrass-Adapted Compost Community, *PLoS One* 2010, 5(1):e8812.
Ban et al., On-Chip Synthesis and Label-Free Assays of Oligosaccharide Arrays, *Angew. Chem.* 2008, 120, 3444-3447; *Angew. Chem. Int. Ed. Engl.* 2008, 47, 3396-3399.
Blanch et al., Addressing the Need for Alternative Transportation Fuels: The Joint BioEnergy Institute, *ACS Chem. Biol.* 2008, 3, 17-20.
Chandrasekaran et al., A Microscale Platform for Integrated Cell-Free Expression and Activity Screening of Cellulases, *Proteome Res.* 2010, 9, 5677-5683.
Chang et al., Glycan array on aluminum oxide-coated glass slides through phosphonate chemistry, *J. Am. Chem. Soc.* 2010, 132, 13371-13380.
Chang et al., Pyranmycins, a Novel Class of Aminoglycosides with Improved Acid Stability: The SAR of d-Pyranoses on Ring III of Pyranmycin, *Org. Lett.* 2002, 4, 4603-4606.

(Continued)

*Primary Examiner* — Amy M Bunker
(74) *Attorney, Agent, or Firm* — Knobbe, Martens, Olson & Bear, LLP

(57) ABSTRACT

Disclosed herein are methods, compositions and systems for analyzing and detecting enzyme activity. For examples, methods, compositions and systems for parallel detection and analysis of enzymatic activities of enzymes in complex biological mixtures are provided.

20 Claims, 14 Drawing Sheets

(56) References Cited

OTHER PUBLICATIONS

Chhabra et al., Regulation of Endo-Acting Glycosyl Hydrolases in the Hyperthermophilic Bacterium Thermotoga maritima Grown on Glucan- and Mannan-Based Polysaccharides, *Appl. Environ. Microbiol.* 2002, 68, 545-554.

Damude, Substrate specificity of endoglucanase A from Cellulomonas fimi: fundamental differences between endoglucanases and exoglucanases from family 6, *Biochem. J.* 1996, 315 (pt 2), 467-472.

Dashtban et al., Fungal Bioconversion of Lignocellulosic Residues; Opportunities & Perspectives, *Int. J. Biol. Sci.* 2009, 5, 578-595.

Datta et al., Ionic liquid tolerant hyperthermophilic cellulases for biomass pretreatment and hydrolysis, *Green Chem.* 2010, 12, 338-345.

DeAngelis et al., Strategies for Enhancing the Effectiveness of Metagenomic-based Enzyme Discovery in Lignocellulolytic Microbial Communities *Bioenergy Research*, 2010, 3, 146-158.

Doi et al., Cellulosomes: plant-cell-wall-degrading enzyme complexes, *Nat. Rev. Microbiol.* 2004, 2, 541-551.

Eckert et al., Gene cloning, sequencing, and characterization of a family 9 endoglucanase (CelA) with an unusual pattern of activity from the thermoacidophile *Alicyclobacillus acidocaldarius* ATCC27009, *Appl. Microbiol. Biotechnol.* 2003, 60, 428-436.

Gardner et al., A Prevotella ruminicola B14 Operon Encoding Extracellular Polysaccharide Hydrolases, *Curr. Microbiol.* 1997, 35, 274-277.

Helenius et al., Intracellular Functions of N-Linked GlycansIntracellular Functions of N-Linked Glycans, *Science* 2001, 291, 2364-2369.

Lee et al., Reactivity-Based One-Pot Synthesis of the Tumor-Associated Antigen N3 Minor Octasaccharide for the Development of a Photocleavable DIOS-MS Sugar Array, *Angew. Chem.* 2006, 118, 2819-2823; *Angew. Chem. Int. Ed. Engl.* 2006, 45, 2753-2757.

Lynd et al., Microbial Cellulose Utilization: Fundamentals and Biotechnology, *Microbiol. Mol. Biol. Rev.* 2002, 66, 506-577.

Mcilvaine et al., A buffer solution for colorimetric comparison, *J. Bioi. Chem.* 1921, 49,183-186.

Northen et al., A nanostructure-initiator mass spectrometry-based enzyme activity assay, *Proc. Natl. Acad. Sci. USA* 2008, 105, 3678-3683.

Northen et al., Clathrate nanostructures for mass spectrometry, *Nature* 2007, 449, 1033-1036.

Pauly et al., Plant cell wall polymers as precursors for biofuels, *Curr. Opin. Plant. Biol.* 2010, 13, 305-312.

Reindl et al., Rapid Screening of Fatty Acids Using Nanostructure-Initiator Mass Spectrometry, *Anal. Chem.* 2010, 82, 3751-3755.

Shallom et al., Microbial hemicellulases, *Curr. Opin. Microbiol.* 2003, 6, 219-228.

Sharrock et al., Cellulase assay methods: a review, *J. Biochem. Biophys. Methods* 1988, 17, 81-105.

Steen et al., Microbial production of fatty-acid-derived fuels and chemicals from plant biomass, *Nature* 2010, 463, 559-562.

Vrsanska et al., An alternative approach for the synthesis of fluorogenic substrates of endo-β-(1→44)-xylanases and some applications, *Carbohydr. Res.* 2008, 343, 541-548.

Wignall et al., Absolute calibration of small-angle neutron scattering data, *J. Appl. Crystallogr.* 1987, 20, 28-40.

Woo et al., Nanostructure-initiator mass spectrometry: a protocol for preparing and applying NIMS surfaces for high-sensitivity mass analysis, *Nat. Protoc.* 2008, 3, 1341-1349.

Reindl et al: "Colloid-based multiplexed screening for plant biomass-degrading glycoside hydrolase activities in microbial communities", The Royal Society of Chemistry, 2011, published on Jun. 30, 2011 on http://pubs.rsc.org | doi:10.1039/C1EE01112J.

Greving et al.: "Acoustic deposition with NIMS as a high-throughput enzyme activity assay", Anal. Bioanal Chem, 2012, DOI 10.1007/s00216-012-5908-8.

Chao: "Berkeley Lab Wins Eight 2013 R&D 100 Awards", Jul. 8, 2013, downloaded from http://newscenter.lbl.gov/2013/07/08/-rd-100-awards/ on Oct. 9, 2014.

Agudo et al., "Achieving Regio- and Enantioselectivity of P450-Catalyzed Oxidative CH Activation of Small Functionalized Molecules by Structure-Guided Directed Evolution," Chembiochern, 13(10):1465-1473 (2012).

Apweiler, et al "Ongoing and future developments at the Universal Protein Resource", Nucleic Acids Res, 39(Suppl 1): D214-D219 (2011).

De Rond et al, "Versatile synthesis of probes for high-throughput enzyme activity screening," Anal. Bioanal. Chem., 405:4969-4973 (2013).

Greving et al., "Acoustic deposition with NIMS as a high-throughput enzyme activity assay", Anal Bioanal Chem, 403(3):707-711 (2012). Epub Mar. 10, 2012.

http://public-registry.jbei.org, part IDs JPUB_000129.

Lee et al., "BglBrick vectors and datasheets: A synthetic biology platform for gene expression", Journal of Biological Engineering 5:12 (2011).

Rostovtsev et al., "A Stepwise Huisgen Cycloaddition Process: Copper(I)-Catalyzed Regioselective "Ligation" of Azides and Terminal Alkynes", Angewandte Chemie International Edition 41 (14): 2596-2599 (2002).

Sails et al., "Automated design of synthetic ribosome binding sites to control protein expression", Nature Biotechnology, 27:946-950 (2009).

Sticklen, MB, Plant genetic engineering for biofuel production: towards affordable cellulosic ethanol, Nat Rev Genet, Jun. 2008; 9 (6): 433-443.

Curran D.P. et al., Thermal Allylations of Aldehydes with a Fluorous Allylstannane. Separation of Organic and Fluorous Products by Solid Phase Extraction with Fluorous Reverse Phase Silica Gel. J Org Chem. (1997) 62:6714-6715 including Supporting Information in 38 pages.

Curran D.P. et al., Fluorous Synthesis with Fewer Fluorines (Light Fluorous Synthesis): Separation of Tagged from Untagged Products by Solid-Phase Extraction with Fluorous Reverse-Phase Silica Gel. J Am Chem Soc. (1999) 121:9069-9072 including Supporting Information in 60 pages.

Matsugi M. et al., Reverse Fluorous Solid-Phase Extraction: A New Technique for Rapid Separation of Fluorous Compounds. Org Lttrs. (2004) 6(16):2717-2720 including Supporting Information in 27 pages.

Smeenk L., Fluorous Solid Phase Extraction—A potential separation method for cysteine or azhal containing peptides from complex mixtures. Master Thesis; Universiteit van Amsterdam (Sep. 2007-Jun. 2008) in 62 pages.

Zhang Q. et al., Separation of "Light Fluorous" Reagents and Catalysts by Fluorous Solid-Phase Extraction: Synthesis and Study of a Family of Triarylphosphines Bearing Linear and Branched Fluorous Tags. J Org Chem. (2000) 65:8866-8873 and Supporting Information in 38 pages.

Zhang W. et al., Synthetic applications of fluorous solid-phase extraction (F-SPE). Tetrahedron. (2006) 62(51):11837-11865.

* cited by examiner

MULTIPLEXED SCREENING OF ENZYME ACTIVITIES USING NANOSTRUCTURE-INITIATOR MASS SPECTROMETRY

CROSS-REFERENCE TO RELATED APPLICATIONS

This application claims priority under 35 U.S.C. § 119(e) to U.S. Provisional Patent Application No. 61/438,586 filed Feb. 1, 2011. The content of this related application is hereby expressly incorporated by reference in its entirety.

STATEMENT OF GOVERNMENT RIGHTS

This invention was made with government support under Contract No. DE-AC02-05CH11231 awarded by the U.S. Department of Energy. The government has certain rights in the invention. This work is a collaboration between inventors at Lawrence Berkeley National Laboratory and Sandia National Laboratories for the Joint BioEnergy Institute.

FIELD OF THE INVENTION

The present application relates to the fields of microbiology, molecular biology, biofuel technology, and biomedicine. More specifically, the present application relates to methods, compositions and systems for analyzing and detecting enzymatic activities.

BACKGROUND

Analysis of enzyme activity and identification of sources of enzyme activity are important in life science technologies. For instance, glycoside hydrolases and transferases (glycohydrolases and glycotransferases) play important roles in a multitude of biological processes, both in eukaryotes (e.g., processing of glycans in glycoproteins) and prokaryotes (e.g., utilization of sugar polymers as carbon source). However, current technology to identify and characterize sources of these enzymes is limited in terms of the ability to resolve complex samples and evaluate large numbers of enzymatic reaction products in parallel. There is a need for efficient methods capable of parallel detection and analysis of enzymatic activities of enzymes in complex biological mixtures.

SUMMARY

The present application relates to methods, compositions, and systems for analyzing and detecting enzymatic activities using substrate analogs and nanostructure-initiator mass spectrometry.

Some embodiments disclosed herein provide a method of detecting the activities of a plurality of enzymes in a multiplexed assay, where the method comprises: incubating a sample with substrates for the plurality of enzymes to obtain reaction products; analyzing the reaction products by nanostructure-initiator mass spectrometry (NIMS); and detecting activities of the plurality of enzymes in the sample by identifying the ratio of substrate-to-reaction product ions in a mass spectrum.

In some embodiments, the plurality of enzymes comprises an enzyme with plant cell wall degrading activity, a lipase, or a protease.

In some embodiments, the enzyme with plant cell wall degrading activity reduces the chain length of a sugar head group. In some embodiments, the sugar comprises cellulose, hemicellulose, xylose, cellobiose, cellotetraose, or xylobiose.

In some embodiments, the enzyme is selected from an endoglucanase, an exoglucanase, a glucosidase, a pectinase, a cellulose, and a hemicellulase. In some embodiments, the enzyme with plant cell wall degrading activity degrades lignin. In some embodiments, the enzyme is a laccase or peroxidase.

In some embodiments, analyzing the reaction product by nanostructure-initiator mass spectrometry (NIMS) comprises applying the reaction product to a hydrophobic NIMS chip surface. In some embodiments, the hydrophobic NIMS chip surface comprises a perfluorinated coating.

In some embodiments, the substrate comprises a substrate head group linked to a perfluorinated tag that forms micelles under aqueous conditions.

In some embodiments, the substrate interacts with the NIMS chip surface via fluorous-phase-interactions.

In some embodiments, the sample is an isolated enzyme or a crude environmental sample. In some embodiments, the sample is obtained by incubating the crude environmental sample with switchgrass or cellulose.

In some embodiments, the reaction products are analyzed in parallel and wherein the reaction products are different in mass. In some embodiments, the reaction products comprise sugar molecules with identical mass and perfluorinated tags of different mass. In some embodiments, the reaction products comprise sugar molecules of different mass and perfluorinated tags of identical mass.

Some embodiments disclosed herein provide a multiplexed system for the activities of a plurality of enzymes, comprising: (i) perfluorinated tagged substrates for the plurality of enzymes; and (ii) a nanostructure-initiator mass spectrometry (NIMS) chip having a surface comprising a perfluorinated coat adapted to interact with the substrates via fluorous-phase-interactions.

In some embodiments, the substrates comprise a cellulose substrate, a hemicelluase substrate, a ligninase substrate, a lipase substrate, a protease substrate, or a combination thereof. In some embodiments, the substrates are tagged with a heptadecafluoro-1,1,2,2-tetrahydrodecyl (F17) tag.

In some embodiments, the NIMS chip surface is coated with bis(heptadecafluoro-1,1,2,2-tetrahydrodecyl)tetramethyl-disiloxane.

BRIEF DESCRIPTION OF THE DRAWINGS

FIG. 1a is a schematic illustration showing enzymatic reactions performed in a multiwall plate in which a reaction well contains a substrate including a sugar head group linked to a hydrophobic perfluorinated tag that forms micelles under aqueous reaction conditions. FIG. 1b is a schematic illustration of samples spotted onto a nanostructure-initiator mass spectrometry (NIMS) chip after enzymatic cleavage. FIG. 1c is a schematic illustration showing vaporization of the initiator by laser irradiation, thereby transferring the applied samples into the gas phase. FIG. 1d is a schematic showing ions of reaction products and uncleaved substrates detected by mass spectrometry.

DETAILED DESCRIPTION

Figure 1:
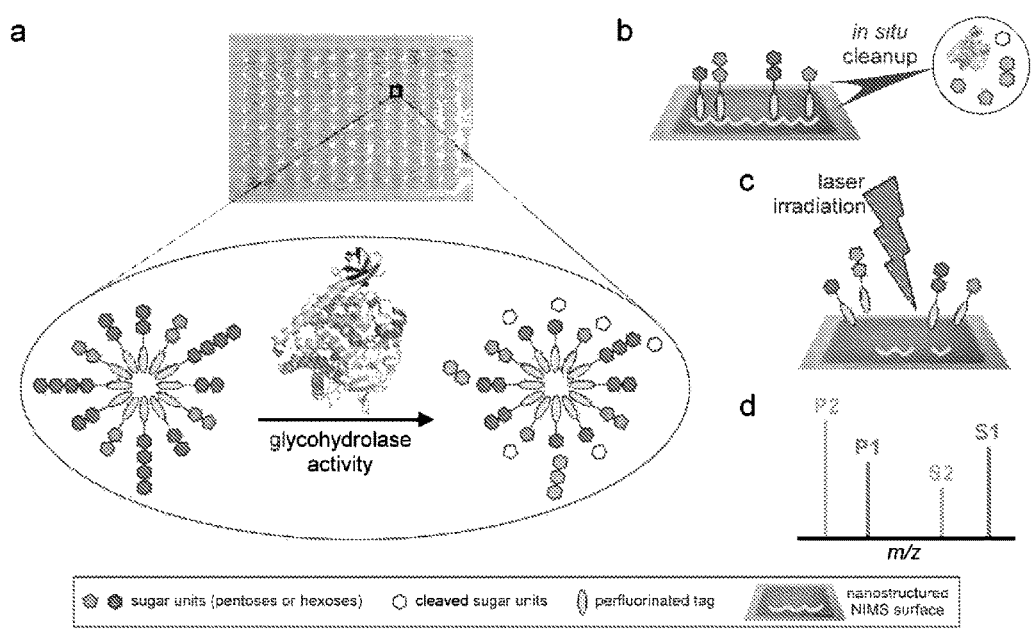
FIG. 1 is a schematic illustration showing one embodiment of a method for detecting enzymatic activity wherein glycohydrolase activity in a sample is identified by a multiplex glycan array.

The description that follows illustrates various embodiments of the subject matter disclosed herein. Those of skill in the art will recognize that there are numerous variations and modifications of the subject matter provided herein that are encompassed by its scope. Accordingly, the description of certain embodiments should not be deemed to limit the scope of the present application.

The present application relates to methods of detecting enzyme activity in a sample. Activities of a plurality of enzymes of interest in a sample can be detected by incubating a sample to be tested for enzymatic activity with substrates for the plurality of enzymes of interest to obtain reaction products, and analyzing the reaction products by nanostructure-initiator mass spectrometry (NIMS). The ratio of substrate-to-reaction product ions in the mass spectrum can be analyzed to determine the activity of one or more enzymes of the plurality of enzymes in the sample, and thus determine the presence of one or more enzymes of interest in the sample.

In some embodiments, glycan substrate analogs are used for the analysis of glycohydrolase or glycotransferase activities. In various aspects, enzymatic reactions using amphiphilic substrates can be carried out, for example, in test tubes or microtiter plates and the reaction product is spotted onto a nanostructured, liquid-coated mass spectrometry chip surface, and analyzed by Nanostructure-Initiator mass spectrometry (NIMS) in a standard MALDI-TOF mass spectrometer.

The methods, compositions and systems described herein can be used in diverse fields such as microbiology, development of biofuels, conversion of biomass, and biomedical applications. For example, the methods, systems, and compositions described herein can provide simultaneous identification and characterization of the enzymatic activities of multiple enzymes (e.g., glycoside hydrolases, lipases and proteases) directly from crude environmental samples. Because enzymatic hydrolysis of polysaccharides into fermentable sugars by glycoside hydrolases is an important step in the conversion of biomass to lignocellulosic biofuels, the methods, systems and compositions described herein are useful for development of biofuels.

Enzymes of Interest

Any enzyme having an activity that changes the mass of a substrate can serve as an enzyme of interest in the embodiments described herein. Non-limiting examples of enzymes of interest include transferases, hydrolases, lyases, and ligases. For example, the transferases can include glycosyltransferases, methyltransferase, acyltransferases sulfurtransferase, and sulfotransferase. Examples of hydrolase include, but are not limited to, lipases, phosphatases, glycoside hydrolases, and proteases.

In some embodiments, the enzyme of interest is involved in sugar modification. For example, the enzyme of interest can have an activity related to changing the chain length of a sugar head group. For example, enzymes of interest include enzymes, that cleave off one or more sugar monomers (glycohydrolases) or enzymes that extend the sugar head group by attaching one or more sugar units (glycotransferases). Examples of enzyme of interest include, but are not limited to, glycohydrolases, glycotransferases, endoglucanases, exoglucanases, and hemicelluases.

In some embodiments, the enzyme of interest is involved in degrading sugar. Non-limiting examples of sugar degrading enzymes of interest include α-amylase; β-amylase; glucan 1,4-α-glucosidase; cellulose; endo-1,3(4)-β-glucanase; inulinase; endo-1,4-β-xylanase, oligo-1,6-glucosidase; dextranase; chitinase; polygalacturonase; lysozyme; exo-α-sialidase; α-glucosidase; β-glucosidase; α-galactosidase; β-galactosidase; α-mannosidase; β-mannosidase; β-fructofuranosidase; α-trehalase; β-glucuronidase; xylan endo-1,3-β-xylosidase; amylo-1,6-glucosidase; hyaluronoglucosaminidase; hyaluronoglucuronidase; xylan 1,4-β-xylosidase; β-D-fucosidase; glucan endo-1,3-β-D-glucosidase; β-L-rhamnosidase; pullulanase; GDP-glucosidase; β-L-rhamnosidase; fucoidanase; glucosylceramidase; galactosylceramidase; galactosylgalactosylglucosylceramidase; sucrose β-glucosidase; α-N-acetylgalactosaminidase; α-N-acetylglucosaminidase; α-L-fucosidase; β-L-N-acetylhexosaminidase; β-N-acetylgalactosaminidase; cyclomaltodextrinase; α-N-arabinofuranosidase; glucuronosyl-disulfoglucosamine glucuronidase; isopullulanase; glucan 1,3-β-glucosidase; glucan endo-1,3-α-glucosidase; glucan 1,4-α-maltotetraohydrolase; mycodextranase; glycosylceramidase; 1,2-α-L-fucosidase; 2,6-β-fructan 6-levanbiohydrolase; levanase; quercitrinase; galacturan 1,4-α-galacturonidase; isoamylase; glucan 1,6-α-glucosidase; glucan endo-1,2-β-glucosidase; xylan 1,3-β-xylosidase; licheninase; glucan 1,4-β-glucosidase; glucan endo-1,6-β-glucosidase; L-iduronidase; mannan 1,2-(1,3)-α-mannosidase; mannan endo-1,4-β-mannosidase; fructan β-fructosidase; agarase; exo-poly-α-galacturonosidase; κ-carrageenase; glucan 1,3-β-glucosidase;

6-phospho-β-galactosidase; 6-phospho-β-glucosidase; capsular-polysaccharide endo-1,3-α-galactosidase; β-L-arabinosidase; arabinogalactan endo-1,4-β-galactosidase; cellulose 1,4-β-cellobiosidase; peptidoglycan β-N-acetylmuramidase; α-phosphotrehalase; glucan 1,6-α-isomaltosidase; dextran 1,6-α-isomaltotriosidase; mannosyl-glycoprotein endo-β-N-acetylglucosaminidase; glycopeptide α-N-acetylgalactosaminidase; glucan 1,4-α-maltohexaosidase; arabinan 1,5-α-L-arabinosidase; mannan 1,4-mannobiosidase; mannan endo-1,6-α-mannosidase; blood-group-substance endo-1,4-β-galactosidase; keratan-sulfate endo-1,4-β-galactosidase; steryl-β-glucosidase; strictosidine β-glucosidase; mannosyl-oligosaccharide glucosidase; protein-glucosylgalactosylhydroxylysine glucosidase; lactase; endogalactosaminidase; mucinaminylserine mucinaminidase; 1,3-α-L-fucosidase; 2-deoxyglucosidase; mannosyl-oligosaccharide 1,2-α-mannosidase; mannosyl-oligosaccharide 1,3-1,6-α-mannosidase; branched-dextran exo-1,2-α-glucosidase; glucan 1,4-α-maltotriohydrolase; amygdalin β-glucosidase; prunasin β-glucosidase; vicianin β-glucosidase; oligoxyloglucan β-glycosidase; polymannuronate hydrolase; maltose-6'-phosphate glucosidase; endoglycosylceramidase; 3-deoxy-2-octulosonidase; raucaffricine β-glucosidase; coniferin β-glucosidase; 1,6-α-L-fucosidase; glycyrrhizinate β-glucuronidase; endo-α-sialidase; glycoprotein endo-α-1,2-mannosidase; xylan α-1,2-glucuronosidase; chitosanase; glucan 1,4-α-maltohydrolase; difructose-anhydride synthase; neopullulanase; glucurono-arabinoxylan endo-1,4-β-xylanase; mannan exo-1,2-1,6-β-mannosidase; α-glucuronidase; lacto-N-biosidase; 4-α-D-{(1→4)-α-D-glucano}trehalose trehalohydrolase; dextrinase; poly(ADP-ribose) glycohydrolase; 3-deoxyoctulosonase; galactan 1,3-β-galactosidase; β-galactofuranosidase; thioglucosidase; β-primeverosidase; oligoxyloglucan reducing-end-specific cellobiohydrolase; xyloglucan-specific endo-β-1,4-glucanase; mannosylglycoprotein endo-β-mannosidase; fructan β-(2,1)-fructosidase; fructan β-(2,6)-fructosidase; oligosaccharide reducing-end xylanase; and the like.

Some embodiments are related to detecting activity of an enzyme involved in degrading plant cell wall material. For example, glycoside hydrolases are important for the development of biofuels from lignocellulosic biomass: long-chain polysaccharides from plant cell walls are enzymatically hydrolyzed and the resulting sugar monomers are fermented into ethanol or advanced biofuels. Three major components forming plant cell walls that are deconstructed include the polysaccharides cellulose and hemicellulose, and the highly phenolic macromolecule lignin. Cellulose is comprised of linear chains of β-1,4-linked D-glucose units, while hemicellulose consists mainly of mixtures of pentoses with D-xylose and D-arabinose being the most abundant. Cellulose is hydrolyzed into glucose through the concerted action of at least three known classes of enzymes collectively referred to as cellulase: endoglucanases, exoglucanases, and β-glucosidases. Without being bound by theory, endoglucanases randomly produce free ends from cellulose fibrils that are further degraded by exoglucanases that release cellobiose, which in turn is hydrolyzed by β-glucosidases into glucose. Hemicelluloses are degraded by a complex class of multi-domain enzymes known as hemicellulases. Lignin gets broken down by "ligninases", e.g. laccases or lignin peroxidases. Some embodiments disclosed herein relate to detection of these enzymes involved in degrading or breaking down plant cell wall.

In several embodiments, the enzyme(s) of interest include cellulase, which includes but is not limited to endoglucanases (endocellulases) for example, endo-1,4-beta-glucanase, carboxymethyl cellulase (CMCase), endo-1,4-beta-D-glucanase, beta-1,4-glucanase, beta-1,4-endoglucan hydrolase, and celludextrinase; exoglucanases (exocellulases); and beta-glucosidases. In several embodiments, the enzymes of interest include cellulase enzymes identified by the Enzyme Commission number EC 3.2.1.4, which is herein fully incorporated by reference in its entirety for examples of enzymes contemplated herein.

In some embodiments, the enzyme(s) of interest include ligninase, which includes but is not limited to lignin peroxidase, manganese peroxidase, laccase, and cellobiose dehydrogenase. In some embodiments, the enzymes of interest include ligninase enzymes identified by the Enzyme Commission number EC 1.14.99, which is herein fully incorporated by reference in its entirety for examples of enzymes contemplated herein.

In some embodiments, the enzyme of interest is involved in catalyzing the formation or hydrolysis of lipids. Examples of lipase include, but are not limited to, Lipase AP4, Lipase AP6, Lipase F-AP15, Lipase OF, Lipase AP12, Lipase M-AP5, Lipase M-AP10, Lipase M-AP20, Lipase Saiken, Lipase PS, Lipase MY, and Lipase B.

In some embodiments, the enzyme of interest is involved in conducting proteolysis. For example, the enzyme of interest can be a protease, such as serine protease, a threonine protease, cysteine protease, an aspartate protease, a metalloprotease, and a glutamic acid protease.

Enzyme Substrates and Substrate Analogs

In some embodiments, enzyme substrates are linked to tags that interact with a surface of a NIMS chip. As used herein, the terms "substrate(s)" and "substrate analog(s)" are used interchangeably and generally refer to a substrate head group linked to a tag. In some embodiments, substrates or substrate analogs include a sugar head group linked to a hydrophobic tag, which is capable of interaction with a hydrophobic NIMS chip surface. For example, substrates can include a sugar head group linked to a perfluorinated tag that interacts with a NIMS chip surface having a perfluorinated coat. Head groups can be sugar monomers, oligomers, or (branched) multimers. In other words, head groups can include monosaccharides, disaccharides, polysaccharides, and oligosaccharides. Examples of monosaccharides, disaccharides, polysaccharides, and oligosaccharides that can be used as head groups in substrate analogs are known in the art. In several embodiments, substrates or substrate analogs can be phenolic substrates degradable by ligninases. Furthermore, a wide range of initiators including but not limited to lauric acid, polysiloxanes, chlorosilanes, methoxy and ethyoxy silanes, fluorous siloxanes, and silanes can be used for NIMS chip surface coating.

Sugars modified by any of the aforementioned enzymes can be linked to a hydrophobic tag and used as substrate analogs in various embodiments of the enzyme activity detection methods described herein. In some embodiments, substrate analogs are based on hexoses, such as cellobiose and cellotetraose, or pentoses, such as xylobiose. Other sugars that can be used as substrate analogs include, without limitation, glucose, fructose, galactose, mannose, maltose, sucrose, lactose, arabinose, xylose, and rhamnose.

In some embodiments, substrates can include a lipid head group linked to a hydrophobic tag, which is capable of interaction with a hydrophobic NIMS chip surface. For example, substrates can include a lipid head group linked to a perfluorinated tag that interacts with a NIMS chip surface having a perfluorinated coat. Head groups can, for example, include lipidic groups or fatty acidic groups. Non-limiting examples of lipidic group group include oleoyl group, stearoyl group, palmitoyl group, lauroyl group, myristoyl group, arachidoyl group, behenoyl group, lignoceoyl group, and the like. In some embodiments, the head group comprises a lipidic group. In some embodiments, the head group comprises a fatty acidic group. In some embodiments, the head group comprises a palmitoyl group.

In some embodiments, substrates can include a polypeptide head group linked to a hydrophobic tag, which is capable of interaction with a hydrophobic NIMS chip surface. For example, substrates can include a polypeptide head group linked to a perfluorinated tag that interacts with a NIMS chip surface having a perfluorinated coat. Head groups can be, for example, a polypeptide. The length of the polypeptide can vary. For example, the polypeptide can have about 1, about 2, about 3, about 4, about 5, about 6, about 7, about 8, about 9, about 10, about 15, about 20, or more amino acids. In some embodiments, the head group has about 9 amino acids. In some embodiments, the head group is a polypeptide comprising one or more Arginine.

A fluorous tag of a substrate analog can be formed by several perfluorinated chemical structures, e.g., aliphatic carbon chains, phenyl rings, etc. For example, fluorinated aliphatic molecules, such as (heptadecafluoro-1,1,2,2-tetrahydrodecyl)-dimethylchlorosilane ("F17") and bis(tridecafluoro-1,1,2,2-tetrahydrooctyldimethylsiloxy)-methylchloro-silane ("F26"), can be used in synthesis of a fluorous tagged substrate. In some embodiments, substrate analogs are tagged with a heptadecafluoro-1,1,2,2-tetrahydrodecyl (F17) tag.

The fluorous tag of a substrate analog can be separated from the substrate head group by a linker. Without being bound by any particular theory, it is believed that the linker can facilitate the accessibility of the substrate head group. The length of the linker can vary. For example, the linker can be a 2-carbon, 3-carbon, 4-carbon, 5-carbon, 6-carbon, 7-carbon, 8-carbon, 9-carbon, 10-carbon, 15-carbon or 20 carbon group. In some embodiments, the linker comprises a five-carbon group, such as 5 methylene group. In some embodiments, the linker comprises an ionization enhancer. As used herein, the term "ionization enhancer" refers to a chemical group that can enhance ionization of the substrate analog during analysis of the enzyme(s) of interest. Non-limiting examples of the ionization enhancer include arginine and dimethyl-arginine.

In some embodiments, substrate analogs are amphiphilic and thus soluble in water or aqueous buffers. Without being bound by any particular theory, dissolving the substrate analogs is possible because they form supramolecular amphiphilic assemblies (e.g., micelles, liposomes, vesicles, colloids, etc.), where the hydrophobic fluorous tail is "shielded" from the aqueous solution, whereas sugar head groups remain accessible for the enzymes' active sites. Therefore, the enzymatic reactions can be performed using the amphiphilic substrate analogs in standard reaction tubes or plates where all reaction conditions can easily be controlled.

Enzymatic Reactions

Enzymatic reactions can be carried out in solution using test tubes or microwell microtiter plates (96-well, 384-well). Enzymatic reactions can be performed using the amphiphilic substrate analogs in standard reaction tubes or plates where all reaction conditions can easily be controlled. Various embodiments described herein involve a solution-based assay system that can be applied to all kinds of standard reaction tubes and microtiter plates. Furthermore, all liquid handling and sample spotting can be interfaced with existing pipetting robots and liquid handling systems, so that several described embodiments are highly suitable for high-throughput applications.

After completing an enzymatic reaction under the desired conditions, reactions can be quenched, e.g., with methanol which denatures all enzymes. For analysis of the occurring enzymatic reactions, small samples volumes (one microliter and below) can be spotted onto the mass spectrometry chip surface. The nanostructured chip can be coated with ultrathin liquid layers of perfluorinated (di)siloxanes. The fluorous tails of the used amphiphilic substrates can interact with this surface via fluorous-phase-interactions, so that substrates are driven down to the chip surface when the sample is spotted. In a "chromatographic" step, all other components of, the reaction sample do not interact with the surface and can be washed away, or simply be pipetted off again, while the substrates stick to the surface. Analysis of enzymatic activities in the mass spectrometer can be performed based on the ratios of substrate-to-product ions, which is advantageous because it is independent from variations of total intensities on various sites on the chip.

Samples

Methods described herein are not limited to detecting activity of purified enzymes, but also include detecting enzyme activity in crude samples like cells, cellular lysates, cellular extracts, and environmental samples. For example, microbial communities (e.g., fungi or bacteria) capable of growing on lignocellulose have gained increasing attention as sources for discovering glycoside hydrolases. As such, several embodiments relate to detecting enzyme activities in samples suspected of containing such microbial communities. Non-limiting examples of samples that can be assayed in several embodiments described herein include plant matter, wood, leaves, paper waste, soil, compost, agriculture waste (e.g. livestock waste), mulch, dirt, clay, and garbage.

In some embodiments, samples are cultivated and extracted for analysis of enzymatic activity using standard techniques available in the field. For example, environmental samples can be inoculated and grown in liquid cultures containing a biomass feedstock such as switchgrass. The supernatants of the liquid cultures can be collected for analysis and detection of enzyme activity as described herein.

Nanostructure-Initiator Mass Spectrometry

In some embodiments, the mass of the reaction product generated by incubating a sample or enzyme with a substrate can be determined by nanostructure-initiator mass spectrometry (NIMS). NIMS is described in T. R. Northen, O. Yanes, M. T. Northen, D. Marrinucci, W. Uritboonthai, J. Apon, S. L. Golledge, A. Nordstrom, G. Siuzdak, *Nature* 2007, 449, 1033-1036; T. R. Northen, J. C. Lee, L. Hoang, J. Raymond, D. R. Hwang, S. M. Yannone, C. H. Wong, G. Siuzdak, *Proc. Natl. Acad. Sci. USA* 2008, 105, 3678-3683; and U.S. Patent Application Publication No. 2008/0128608, which are herein fully incorporated by reference. Production of NIMS chips is described in detail in H. K. Woo, T. R. Northen, O. Yanes, G. Siuzdak, *Nat. Protoc.* 2008, 3, 1341-1349, which is herein fully incorporated by reference. The ratio of substrate-to-reaction product ions in the mass spectrum can be analyzed to determine the presence of the enzyme of interest in the sample.

A variety of apparatuses can be used in NIMS to measure the mass-to-charge ratio of the ionized target. For example, in several embodiments a time-of-flight mass analyzer is used for measuring the desorbed and ionized target. However, other non-limiting examples of mass analyzers that can be used include magnetic ion cyclotron resonance instruments, deflection instruments, and quadrupole mass analyzers.

Thus, the methods and apparatuses described herein permit parallel detection of large numbers of reaction products based on the substrates and reaction products differing in mass. Some embodiments disclosed herein relate to enzyme activity detection involving parallel use of pentose and hexose-based substrates. Substrate analogs including head groups with identical masses can be used by linking them to tags of different mass. For example, polysaccharides with identical masses (e.g., cellobiose and maltose) can be analyzed in parallel by using different chemical structures in the linker or tags of varying length. Accordingly, some embodiments described herein allow simultaneous testing of a plurality of samples and enzymatic reactions without analytical interference.

The above description discloses several methods and materials of the present invention. This invention is susceptible to modifications that will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention. All references cited herein are incorporated by reference in their entirety and are hereby made a part of this specification.

Methods for Detecting Enzymatic Activity

Some embodiments disclosed herein provide a method of detecting the activities of a plurality of enzymes in a multiplexed assay. The method, in some embodiments, allows simultaneous detection of the activities of multiple enzymes. For example, the activities of two, three, four, or more enzymes may be detected simultaneously by the method.

In some embodiments, the method includes incubating a sample with substrates for the plurality of enzymes to obtain reaction products, analyzing the reaction products by nanostructure-initiator mass spectrometry (NIMS); and detecting activities of the plurality of enzymes in the sample by identifying the ratio of substrate-to-reaction product ions in a mass spectrum. The activity of the enzyme, in some embodiments, correlate with the ratio of substrate-to-reaction product ions. In some embodiments, the activity of the enzyme negatively correlates with the ratio of substrate-to-reaction product ions. As described above, NIMS is described, for example, in US Patent Publication 20080128608, which is hereby expressly incorporated by reference.

In some embodiments, applying the reaction product can be applied to a hydrophobic NIMS chip surface for analyzing the reaction product. The hydrophobic NIMS chip surface can, for example, include a perfluorinated coating. In some embodiments, the substrate comprises a substrate head group linked to a perfluorinated tag that forms micelles under aqueous conditions. In some embodiments, the substrate interacts with the NIMS chip surface via fluorous-phase-interactions.

The methods disclosed herein can, in some embodiments, analyze the reaction products in parallel. In some embodiments, the reaction products are different in mass. In some embodiments, the reaction produces comprise sugar molecules with identical mass and perfluorinated tags of different mass. In some embodiments, the reaction products comprise sugar molecules of different mass and perfluorinated tags of identical mass. In some embodiments, the reaction products comprise amino acid molecules with identical mass and perfluorinated tags of different mass. In some embodiments, the reaction products comprise amino acid molecules of different mass and perfluorinated tags of identical mass.

Systems for Detecting Plant Cell Wall Degrading Enzymatic Activity

Some embodiments are drawn to systems for detecting plant cell wall degrading enzymatic activity. A system for detecting plant cell wall degrading enzymatic activity can include any of the above-described substrates and NIMS chips. For example, a system for detecting plant cell wall degrading enzyme activity can include a tagged xylobiose, cellobiose, or cellotetraose substrate, or combinations thereof, and a NIMS chip having a surface which includes a tag capable of interacting with the substrate. In some embodiments, the substrate(s) have a fluorous tag and the NIMS chip surface is coated with a fluorous initiator that is capable of interacting with the tag. For example, a system for detecting plant cell wall degrading activity can include a substrate, such as but not limited to xylobiose, cellobiose, cellotetraose, or combinations thereof tagged with a heptadecafluoro-1,1,2,2-tetrahydrodecyl (F17) tag and a NIMS chip having a surface coated with bis(heptadecafluoro-1,1,2,2-tetrahydrodecyl)tetramethyl-disiloxane. In some embodiments, systems for detecting plant cell wall degrading enzymatic activity further include a sample such as a crude environmental sample suspected of having the enzyme activity of interest.

EXAMPLES

Having generally described embodiments of the present application, a further understanding can be obtained by reference to certain specific examples which are provided herein for purposes of illustration only, and are not intended to be limiting.

Example 1

Self-assembled colloids and NIMS for the multiplexed identification and characterization of glycoside hydrolase activities are described in this Example.

FIG. 1 shows a schematic illustration of one embodiment of a method for detecting enzymatic activity, wherein glycohydrolase activity in a sample is identified by a multiplex glycan array. As illustrated in FIG. 1a, enzymatic reactions can be performed in a multiwall plate in which a reaction well contains a substrate including a sugar head group linked to a hydrophobic perfluorinated tag that forms micelles under aqueous reaction conditions. The samples can then be spotted onto a nanostructure-initiator mass spectrometry (NIMS) chip after enzymatic cleavage (FIG. 1b). As shown in FIG. 1c, the initiator can be vaporized by laser irradiation, thereby transferring the applied samples into the gas phase. And then, ions of reaction products and uncleaved substrates can be detected by mass spectrometry (FIG. 1d).

Figure 2:
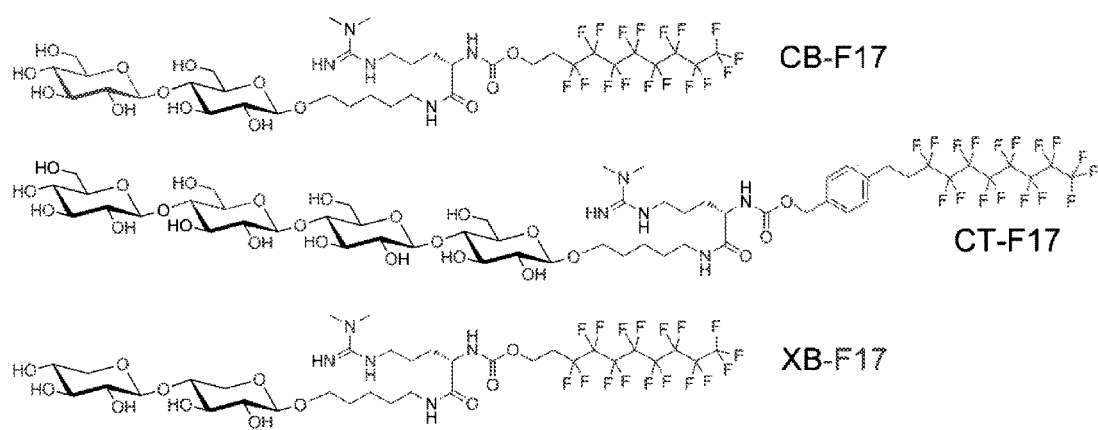
FIG. 2 is an illustration of various exemplary substrates that contain a sugar head group coupled to a perfluorinated heptadecafluoro-1,1,2,2-tetrahydrodecyl (F17) tag.
Figure 3:
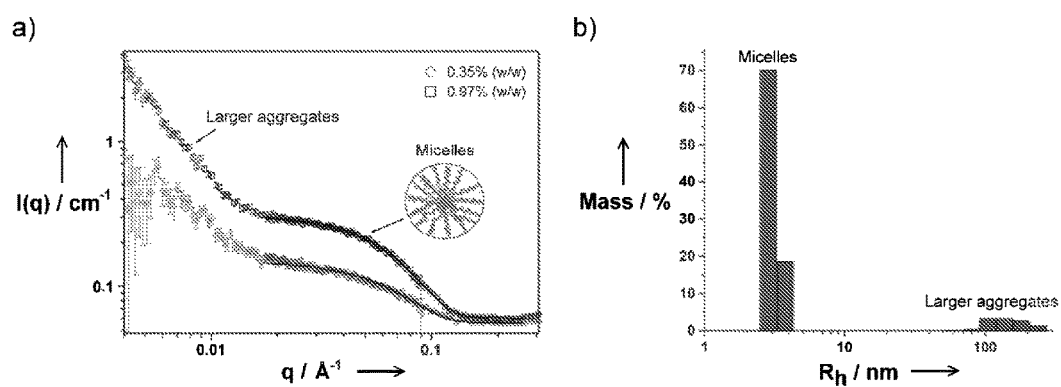
FIG. 3a is a small-angle neutron scattering curve showing colloid formation of cellobiose (CB-F17).
FIG. 3b is a graph showing the size distribution of the hydrodynamic radius for cellobiose (CB-F17).

Assays were performed with amphiphilic substrate analogs comprising a polar sugar head group and a highly hydrophobic perfluorinated tail (F17) (FIG. 2). The sugar groups used in this study were based on hexoses, such as cellobiose (CB) and cellotetraose (CT), or pentoses, such as xylobiose (XB). Due to their amphiphilic character, substrates spontaneously formed colloids, as identified for CB-F17 by small-angle neutron scattering (SANS) and dynamic light scattering (DLS). As shown in FIG. 3a-b, both SANS and DLS techniques showed a consistent radius for the detected main particles: 27.5 Å (polydispersity 14%) for SANS and 30.0 Å (polydispersity 12%) for DLS. Additionally, SANS measurements revealed a spherical shape for the particles (FIG. 3a). With an estimated molecule size of ~24 Å for CB-F17, the recorded diameters of ~55-60 Å and the spherical shape suggest the formation of micelles (FIG. 3a-b). Thus, despite containing a large hydrophobic moiety, substrates could be dissolved in aqueous solutions, allowing enzymatic reactions to be performed in standard buffers and labware. After enzymatic cleavage, samples could be spotted directly onto a NIMS surface without any further sample preparation steps, even if they contained crude environmental extracts with visible particles. This is due to the fact that the substrates selectively bind to the surface via fluorous-phase-interactions, while other sample components (i.e. enzymes, cleaved off sugar units, salts) can be washed away in situ, which enhances signal intensities. Therefore, the assay system comprises the benefits of sample purification, while requiring only a minimal fraction of time in comparison to standard chromatography techniques. Once spotted onto the NIMS surface, samples were stable for several weeks.

Figure 4:
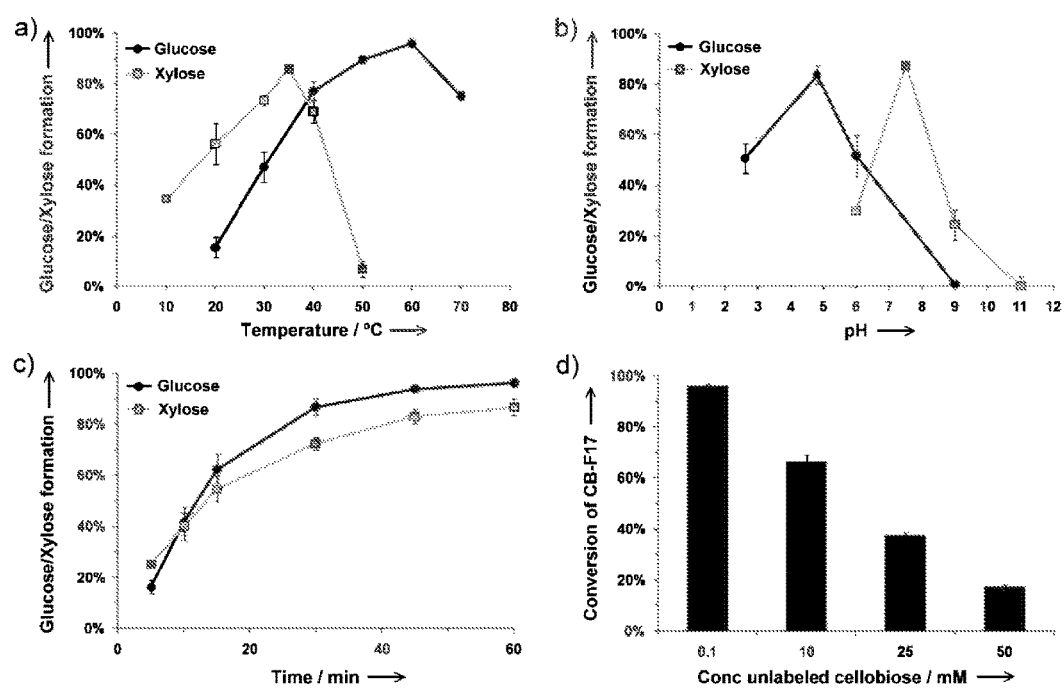
FIG. 4a is a line graph showing the temperature optima for β-glucosidase and β-xylosidase.
FIG. 4b is a line graph showing the pH optima for β-glucosidase and β-xylosidase.
FIG. 4c is a line graph showing activity of β-glucosidase and β-xylosidase over time.
FIG. 4d is a bar graph showing competition between CB-F17 and unlabeled cellobiose for conversion by β-glucosidase.

The next step was the analysis by NIMS in a MALDI mass spectrometer, where laser irradiation leads to vaporization of the initiator liquid on the chip surface and subsequent transfer of applied samples into the gas phase. Acquired spectra show pairs of substrate and product signals, such that enzymatic activities can be measured as product-to-substrate ratios, which is completely independent from total signal intensities. This method was validated by analyzing commercially available β-glucosidase and β-xylosidase activities using cellobiose (CB-F17) or xylobiose (XB-F17) as substrates in separate setups (FIG. 4): determined temperature and pH optima for both enzymes match the known reaction optima for these enzymes as specified by the manufacturers; additionally, kinetic and competition studies could be performed.

Figure 5:
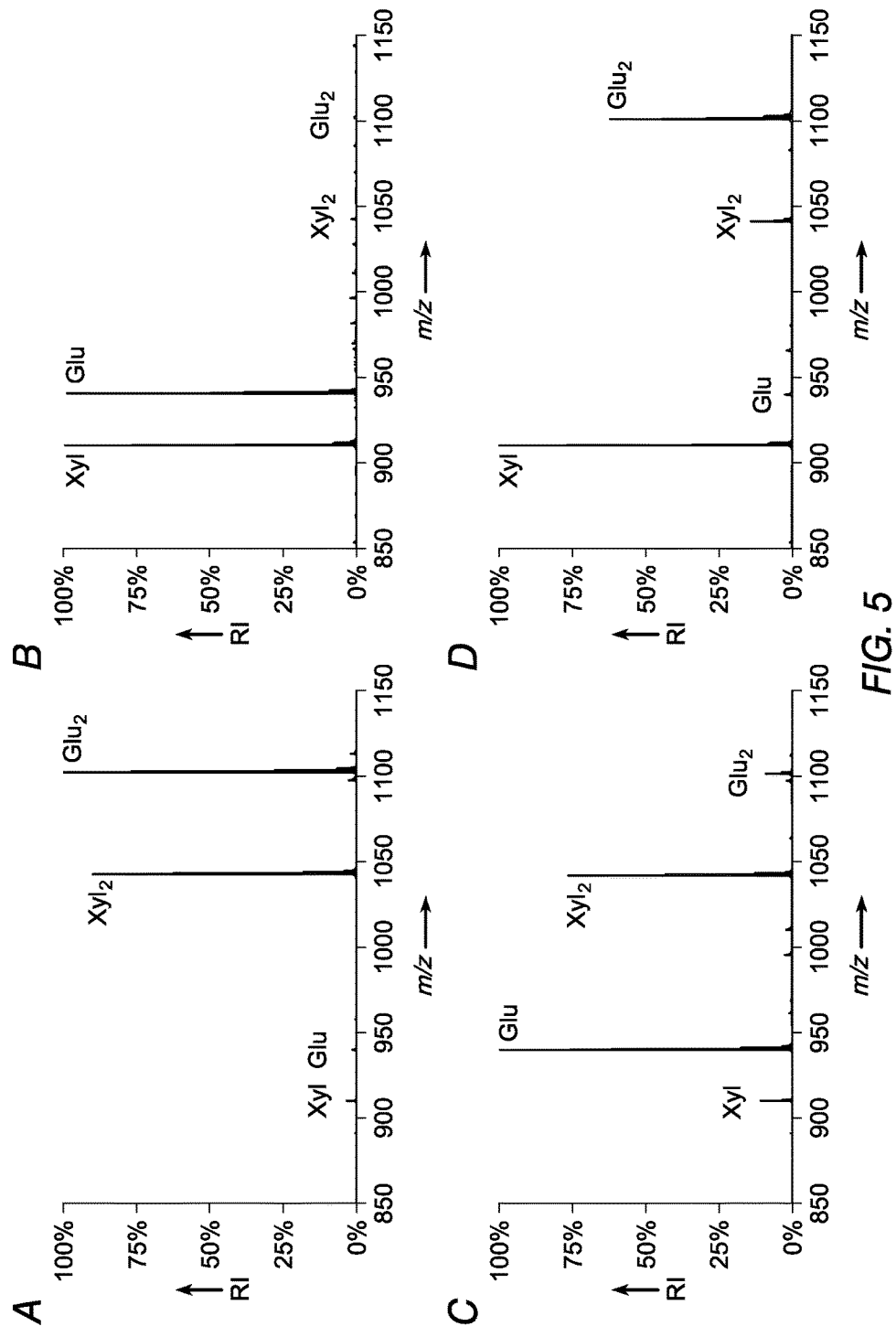
FIG. 5 is a mass spectrum showing signals for xylose (FIG. 5a), glucose (FIG. 5b), xylobiose (FIG. 5c), and cellobiose (FIG. 5d).

It can be difficult to discriminate between several products in simultaneous reactions using conventional spectroscopic methods since these reactions typically yield the same outputs and there are only a few unique absorption or emission patterns that can be resolved separately. In contrast, mass spectrometry can resolve thousands of ions and therefore we have discovered that it is well-suited for the parallel detection of large numbers of reaction products where the substrates and occurring products differ in mass. This is the case, for example, when using pentose and hexose-based substrates at the same time. The hydrolysis of polysaccharides with identical masses (e.g. cellobiose and maltose) can even be analyzed in the same run by using different chemical structures in the linker or perfluorinated tags of varying length. Thus, potentially dozens of enzymatic conversions can be tested simultaneously using this method. Here both β-glucosidase and β-xylosidase activities were detected simultaneously utilizing a substrate cocktail comprised of equal amounts of CB-F17 and XB-F17. In the non-enzyme control only signals for cellobiose and xylobiose were detectable (FIG. 5a). Incubation of the two substrates with a β-glucanase/xylanase enzyme cocktail lead to complete cleavage of both (FIG. 5b). After incubation with β-glucosidase, cellobiose was almost completely converted to glucose, while there was only a slight increase in the xylose signal, probably due to side reactions of the enzyme (FIG. 5c). For β-xylosidase there was conversion of xylobiose to xylose and no enzymatic cleavage of cellobiose (FIG. 5d). These data demonstrate the applicability of this method for the analysis of several glycoside hydrolase activities in parallel.

Enzyme Activity Assays

The β-glucosidase (NS50010) and the β-glucanase/xylanase mixture (NS22002) were part of the 'Biomass Kit' from Novozymes (Davis, Calif.). 1,4-β-D-xylosidase from Bacillus pumilus was purchased from Megazyme (Wicklow, Ireland). Two different expression versions of the exoglucanase Cs_GH5 from *Caldicellulosiruptor saccharolyticus*, the endoglucanases Pr_GH5 from *Prevotella ruminicola*, Cel5A from *Thermotoga maritima*, and Cel9A from *Alicyclobacillus acidocaldarius* were kindly provided by Joshua Park and Supratim Datta (Joint BioEnergy Institute, Emeryville, Calif., USA). An additional undisclosed β-glucosidase (UBG) was also included.

Separate Analysis of β-Glucosidase and β-Xylosidase Activity

The separate characterization of β-glucosidase and β-xylosidase activity was carried out in reaction volumes of 20-50 μL, by mixing 0.1 mM cellobiose with 8 μg of NS50010 in 50 mM sodium acetate buffer (pH 4.8), or 0.1 mM xylobiose with 0.13 μg (in 20 mL) or 0.33 μg (in 50 μL) of 1,4-β-D-xylosidase in 50 mM potassium phosphate buffer (pH 7.5) with 1 mg/mL BSA. For the competition studies with cellobiose, samples additionally contained 10, 25, or 50 mM of unlabeled cellobiose (Sigma-Aldrich; St. Louis, Mo.). Other buffers used for the determination of the pH optima were McIlvaine's citrate/phosphate buffer (pH 2.6 and 6.0), 50 mM Tris buffer (pH 9.0) for NS50010, and 50 mM potassium phosphate buffer (pH 6.0), 50 mM Tris buffer (pH 9.0), 50 mM sodium borate buffer (pH 11.0), all with 1 mg/mL BSA for the β-xylosidase. Samples were incubated for 1 h at 35° C. (β-xylosidase) or 50° C. (NS50010), for determination of temperature optima samples were additionally incubated at the given temperatures. Reactions were quenched by adding one sample volume of ice-cold methanol. For monitoring the enzymatic reactions over time, small aliquots were taken out of a bigger reaction volume at the given time points, quenched by adding one aliquot volume of methanol, and kept on ice until further analysis.

Multiplexed β-Glucosidase/β-Xylosidase Assay

For the simultaneous analysis of β-glucosidase and β-xylosidase activity a mixture of 0.1 mM cellobiose and 0.1 mM xylobiose was incubated with 8 μg NS50010 in 50 mM sodium acetate buffer (pH 4.8), with 6.5 μg β-xylosidase in 50 mM potassium phosphate buffer (pH 7.5) with 1 mg/mL BSA, or with 2.4 mg NS22002 in 50 mM sodium acetate buffer (pH 6.0) in a total reaction volume of 20 μL each. Samples were incubated for 1 h at 35° C. (β-xylosidase) or 50° C. (NS50010 and NS22002). Reactions were quenched by adding one sample volume of ice-cold methanol.

Characterization of β-Glucosidase, Exoglucanase, and Endoglucanase Activity

To assess the spectrum of potentially catalyzed reactions by the three different groups of cellulose degrading enzymes, two β-glucosidases, two exoglucanases, and three endoglucanases were incubated for 15 min with 0.02 mM cellotetraose in a total reaction volume of 25 μL. The used enzymes, buffers and temperatures are shown in Table 1. All enzymes were used, at their optimal reaction temperatures. Reactions were quenched by adding one sample volume of ice-cold methanol.

TABLE 1

Overview of enzymes and reaction conditions

| Enzyme name | Enzyme type | Enzyme amount | Buffer | Temp |
|---|---|---|---|---|
| NS50010 | β-glucosidase | 1.2 mg | 10 mM sodium acetate (pH 4.8) | 50° C. |
| UBG | β-glucosidase | 2 μg | McIlvaine's citrate/phosphate buffer (pH 7.0)[13] | 50° C. |
| Cs_GH5-1 | exoglucanase | 2.9 μg | McIlvaine's citrate/phosphate buffer (pH 6.0)[13] | 80° C. |
| Cs_GH5-2 | exoglucanase | 3.2 μg | McIlvaine's citrate/phosphate buffer (pH 6.0)[13] | 80° C. |
| Pr_GH5 | endoglucanase | 3.8 μg | McIlvaine's citrate/phosphate buffer (pH 6.0)[13] | 37° C. |
| Cel5A | endoglucanase | 1.9 μg | McIlvaine's citrate/phosphate buffer (pH 6.0)[13] | 80° C. |
| Cel9A | endoglucanase | 12.5 μg | McIlvaine's citrate/phosphate buffer (pH 6.0)[13] | 70° C. |

Example 2

Figure 6:
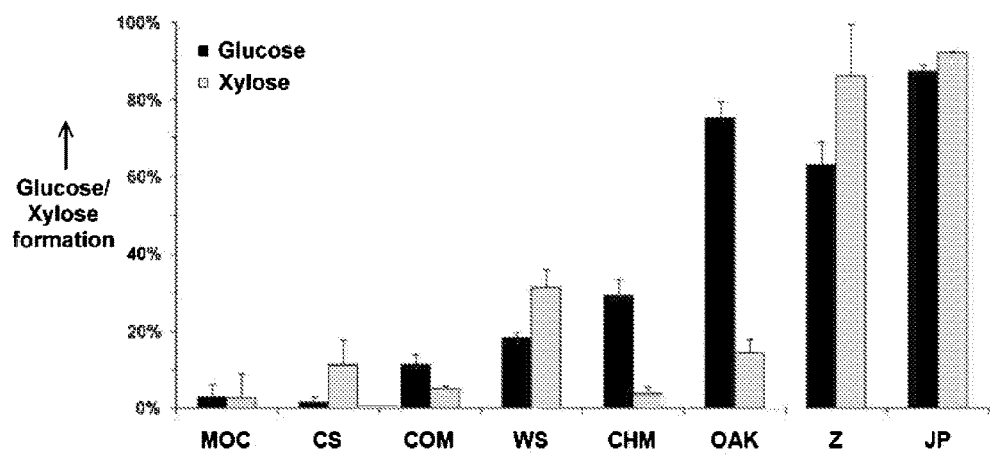
FIG. 6 is a bar graph showing β-glucosidase and β-xylosidase activities in eight environmental samples.

The described nanostructure-initiator mass spectrometry (NIMS)-based method was capable of identifying and characterizing multiple glycoside hydrolase activities directly from crude environmental samples. The multiplexed assay system was used for screening for potential glycoside hydrolase activities in environmental samples. The following workflow was applied for obtaining these samples: soil samples were collected at various sites with different soil characteristics; a small amount of each sample was used to inoculate minimal growth medium with switchgrass as sole carbon source; after one week of incubation the remaining soil particles were removed by centrifugation and the resulting supernatants containing secreted enzymes (secretome) from the present microbial community were used for further analysis. The secretomes of the environmental samples were incubated with a mixture of equal amounts of CB-F17 and XB-F17 for 1 hour at 50° C. and analyzed for conversion of these substrates. This approach proved to be very effective, and at least one of the targeted activities was detected in the majority of samples tested, while several samples showed clear substrate conversion for both targeted enzymatic activities (FIG. 6). The Jepson Prairie (JP) compost sample was the most effective in terms of overall liberation of monomeric sugars with 87.1%±2.1% cellobiose and 92.3%±0.4% xylobiose conversion.

Figure 7:
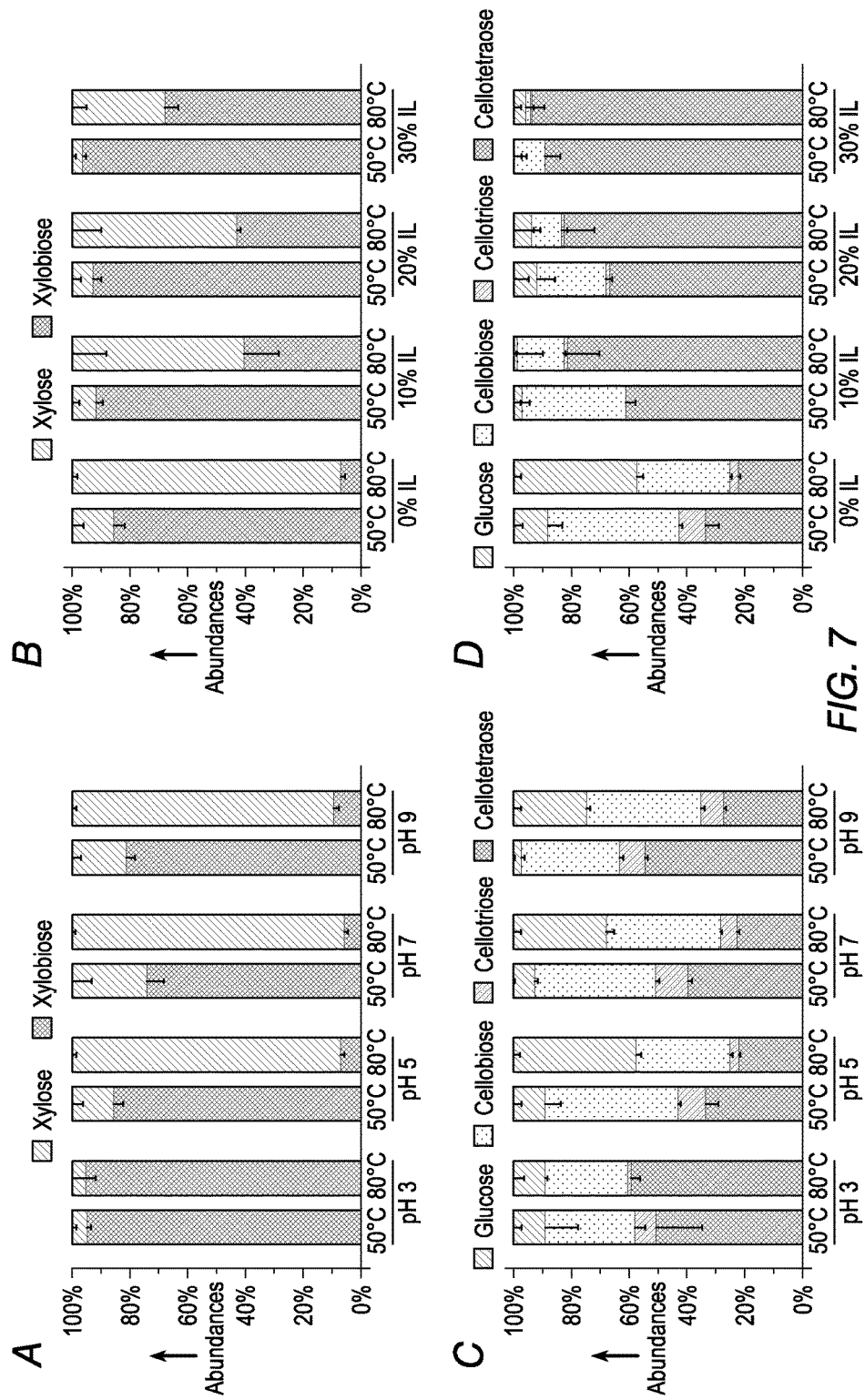
FIG. 7a is a bar graph showing xylanase activity present in a Jepson Prairie compost sample under a range of pH condition.
FIG. 7b is a bar graph showing xylanase activity present in a Jepson Prairie compost sample under a range of ionic liquid (IL) conditions.
FIG. 7c is a bar graph showing cellulase activity present in a Jepson Prairie compost sample under a range of pH conditions.
FIG. 7d is a bar graph showing cellulase activity present in a Jepson Prairie compost sample under a range of ionic liquid (IL) conditions.

For a detailed multiplexed characterization of the JP secretome, the extract was incubated with a mixture of XB-F17 and CT-F17 for 30 min at 50° C. or 80° C. at pH 3, 5, 7, and 9, and in the presence of 0%, 10%, 20%, and 30% ionic liquid (IL; ethyl-3-methyl imidazolium (EMIM) acetate). The ionic liquid reagent is a molten salt used for pretreatment of biomass, and IL-tolerance is highly desirable for enzymes and microbes involved in biomass degradation. The β-xylosidase activity showed a clear preference for higher temperatures under every reaction condition tested, suggesting that the β-xylosidase(s) present in the JP secretome are thermophilic enzymes (FIGS. 7a and 7b). Essentially no β-xylosidase activity was detected at pH 3, while XB-F17 was converted at pH 5, 7, and 9. At 80° C. more than 90% of XB-F17 was degraded at pH 5, 7, and 9. The 50° C. data show a pH optimum at around pH 7 (FIG. 7a). The IL profile of β-xylosidase activity revealed that these enzymes have a surprisingly strong IL-tolerance. Even at 30% IL 32.3%±4.2% of XB-F17 was hydrolyzed at 80° C. (FIG. 7b).

Figure 8:
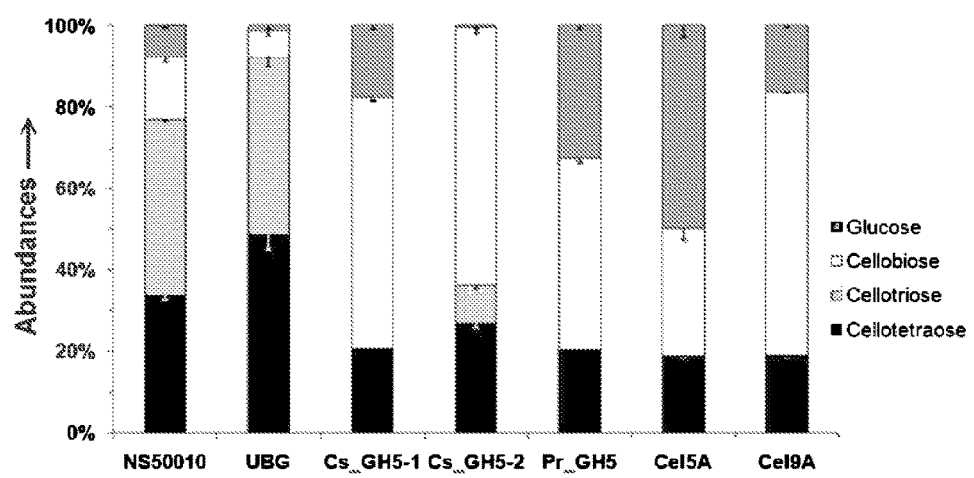
FIG. 8 is a bar graph showing activities of control enzymes on glucose, cellobiose, cellotriose and cellotetraose.

The cellulase activity in the secretome was also highest at 80° C. (FIG. 7c), showing that the cellulase enzymes are thermophilic, as well. Strong cellobiose and glucose signals suggest that the JP secretome is composed primarily of exo- and endoglucanases, as it showed an activity pattern comparable to exo- and endoglucanase control enzymes (FIG. 8). However, as no triose formation was observed for the control exo- and endoglucanases, but for control β-glucosidases (FIG. 8) and a significant amount of triose was detected for the JP secretome (FIG. 7c), this indicates that the secretome also contains β-glucosidases. The pH optimum for cellulase activity was determined to be at pH 5 (FIG. 7c). In contrast to the β-xylosidases, the cellulases were much less IL-tolerant. At 50° C., there was hardly any detectable cellulase activity at 30% IL, with 89.6%±5.1% of the CT-F17 substrate remaining (FIG. 7d). Surprisingly, the limited tolerance was greater at 50° C. than 80° C. Without being bound by theory, we hypothesize that the particular reaction leading to the inactivation of the affected glycoside hydrolase(s) is kinetically favored at higher temperatures.

Thus, this approach was found to screen major classes of lignocellulolytic enzymes (β-glucosidases, exo-/endoglucanases, and β-xylosidases) from a range of relevant sample types for the development of sustainable biofuels. For a more comprehensive analysis of plant cell wall degradation, several more substrates can be used for the analysis of additional enzymatic activities. Longer β-1,4-linked glucose chains can be used to study endoglucanases in more detail, longer xylose chains or also other sugars, such as arabinose or mannose, can be used to aid in the identification and characterization of hemicellulases, and phenolic substrates can be used to study lignin degradation.

Analysis of Environmental Samples

Environmental Samples.

Two commercially available compost samples and four soil samples collected at various sites in Berkeley, Calif. or Walnut Creek, Calif. were used: cow (COM) and chicken (CHM) manure, soil mixed with leafs from under an oak tree (OAK), clay-rich soil (CS), mixed organic compost (MOC), and a sample from light woodland (WS). These samples were manually fragmented with a hammer. Additionally two samples collected from two different green waste compost sites in northern California were included: Zamora (Z) and Jepson Prairie (JP). The latter compost sample was collected at the Jepson Prairie Organics facility (Vacaville, Calif.). This facility processes municipal green waste in turned and watered windrows. Compost was collected from 7, 30, and 60 day windrows. The 7 day windrow was in the mesophilic stage of composting and slightly warm to the touch. The 30 and 60 day windrows were in the thermophilic composting stage, hot to the touch, and steaming. The top 12 inches of each windrow was removed with a spade and the exposed biomass underneath was packed into 50 ml tubes, stored at room temperature during transport, and then frozen at −80° C.

Cultivation and Extraction of Environmental Samples.

200 mg of small fragments (<3 mm$^3$) of each of the eight environmental samples were used to inoculate 50 mL liquid cultures containing 1 g of extracted switchgrass (washed exhaustively with water and ethanol in a soxhlet apparatus) in M9 minimal medium with trace elements (M9TE). Cultures were incubated at 60° C. with shaking at 200 rpm for one week. Two mL of each sample was then collected: each sample was placed in a 2 mL tube, spun at 21,000×g for 5 minutes, the supernatant containing secreted enzymes (secretome) was aliquoted to a new tube, and stored at 4° C. till further use in enzymatic activity assays.

The Jepson Prairie (JP) compost sample was also used to generate switchgrass-adapted thermophilic consortia. Briefly, JP was used to inoculate liquid cultures containing switchgrass as the sole carbon source and grown at 60° C. The compost-derived microbial communities were allowed to adapt to switchgrass in liquid culture for a total of 32 weeks (16×2 week passages). After adaptation, the supernatants (JP SG secretome) of the liquid cultures were collected for enzyme assays as described below. An additional liquid culture was established using 2 ml of passage #15 of the JP switchgrass-adapted culture to inoculate a culture containing 50 mL of M9TE and 0.5 g of microcrystalline cellulose (Sigma-Aldrich; St. Louis, Mo.). This culture was incubated for two weeks at 60° C. with shaking at 200 rpm. Ten ml of the culture was placed into five 2 mL tubes, spun at 21,000×g for 5 minutes, the supernatant (JP MC secretome) was collected and filtered through a 0.2 µm filter, and stored at 4° C. until used in enzyme assays.

Screening for β-Glucosidase/β-Xylosidase Activity.

For the detection of glycoside hydrolase activity a mixture of 0.02 mM cellobiose and 0.02 mM xylobiose were mixed with 75% (v/v) per environmental sample secretome in 50 mM sodium acetate buffer (pH 5.0). The total reaction volume was 30 µL. Samples were incubated for 1 h at 50° C. and reactions quenched by adding four reaction volumes of ice-cold methanol.

Enzymatic Profiling of the JP MC Environmental Sample.

For analysis of the activity profile of cellulose-degrading glucoside hydrolase(s) and β-xylosidase(s) of the JP MC sample a mixture of 0.006 mM cellotetraose and 0.01 mM xylobiose were mixed with 42% (v/v) of the JP MC secretome. For determination of the pH profile reactions were carried out in McIlvaine's citrate/phosphate buffer (pH 3.0, 5.0, 7.0) or 10 mM Tris buffer (pH 9.0). For determination of the ionic liquid (IL) tolerance 0%, 10%, 20%, or 30% (v/v) ethyl-3-methyl imidazolium (EMIM) acetate (Sigma-Aldrich; St. Louis, Mo.) were added to the sample in McIlvaine's citrate/phosphate buffer (pH 5.0). All samples were incubated for 30 min at 50° C. and 80° C. Reactions were quenched by adding one sample volume of ice-cold methanol.

Example 3

Measuring Colloid Formation.

In FIG. 3a, Small-angle neutron scattering (SANS) curves were acquired for 0.35% (w/w) and 0.97% (w/w) cellobiose (CB-F17) in $D_2O$. Scattering intensity was proportional to solution concentration. The upturn in the low q range of $0.004 < q < 0.017$ Å$^{-1}$ indicated the presence of large aggregates. Following the low q upturn, a plateau was clearly observed over a wide q range, which indicated that clusters had a minor influence on the scattering in the higher q regime and only a small fraction of the mass belonged to the larger aggregates. The scattering in the intermediate q range of $0.017 < q < 0.15$ Å$^{-1}$, corresponded to the scattering from individual colloids/micelles whereas in the high q range of $0.15 < q < 0.3$ Å$^{-1}$ it came from incoherent background scattering of the solutions. A form factor of a uniform sphere was used to fit the SANS data in the intermediate q range (solid lines). The main particle radius was determined to be 27.5 Å (polydispersity 14%). The cartoon depicts a schematic micelle. In FIG. 3b, size distribution of the hydrodynamic radius (Rh) determined by dynamic light scattering (DLS) for 0.35% (w/w) cellobiose (CB-F17) in $D_2O$ shows a Rh of 30.0 Å (polydispersity 12%) for the detected main particles and a small amount (11% of total mass) of larger aggregates with a radius of ~148 nm (polydispersity 36%).

Measuring Colloid Formation

Small-Angle Neutron Scattering (SANS).

SANS experiments were conducted on a CG2 (GP-SANS) instrument with a neutron wavelength of $\lambda = 4.8$ Å ($\Delta\lambda/\lambda \sim 0.14$). Liquid solutions of 0.35% (w/w) and 0.97% (w/w) CB-F17 in $D_2O$ were put into 1 mm quartz cells. Measurements were carried out at room temperature. Two sample-detector distances were used (4.0 and 14 m with a 40 cm detector offset), which resulted in a range of 0.004 Å$^{-1} \leq q \leq 0.3$ Å$^{-1}$ for the scattering vector q ($=4\pi \sin \theta/\lambda$). The data was corrected for instrumental background as well as detector efficiency and put on absolute scale (cross section I(q) per unit volume in units of cm$^{-1}$) by means of precalibrated secondary standard Dynamic Light Scattering (DLS).

DLS experiments were performed at 25° C. with a 0.35% (w/w) solution of CB-F17 in $D_2O$ on a DynaPro plate reader (Wyatt Technology; Santa Barbara, Calif.) with a wavelength of 832.6 nm and a detection angle of 158°. The size distribution was obtained by analyzing the auto correlation function using regularization analysis.

Example 4

Method Validation with Known Enzymes.

In FIG. 4a, the determined temperature optima for the used enzymes were 50-60° C. for β-glucosidase (black) and 35° C. for β-xylosidase (gray). In FIG. 4b, the determined pH optima were around pH 4.8 for β-glucosidase (black) and around pH 7.5 for β-xylosidase (gray). FIG. 4c shows monitoring β-glucosidase (black) and β-xylosidase (gray) activity over time. Kinetic studies were performed by analyzing aliquots of each reaction sample at the given time points. In FIG. 4d, product inhibition was studied by analyzing β-glucosidase activity in the presence of untagged cellobiose. As expected, there was competition for conversion with increasing amounts of non-perfluorinated cellobiose with an $IC_{50}$ of about 15-20 mM at the used assay conditions. All activities were corrected by the values of negative control samples without enzyme. Error bars represent standard deviation of three independent experiments.

Example 5

Assessment of Activities of Control Enzymes.

In FIG. 8, for an analysis of the polysaccharide degrading capabilities of cellulases, pure β-glucosidases (NS50010, UBG), exoglucanases (Cs_GH5-1, Cs_GH5-2), and endoglucanases (Pr_GH5, Cel5A, Cel9A) were incubated with perfluorinated cellotetraose (CT-F17) as substrate. All activities were corrected by the values of negative control samples without enzyme. Error bars represent standard deviation of three independent experiments.

Bars 1-2: Both β-glucosidases were able to stepwise degrade CT-F17 from the tetraose to cellotriose, cellobiose, and glucose. The preferred reaction of β-glucosidases is the conversion of cellobiose to glucose, but the production of sugar monomers from longer cellodextrins is also catalyzed, presumably at a slower reaction speed. The most abundant signal for both β-glucosidases was cellotriose, followed by cellobiose and glucose.

Bars 3-7: The main reaction for exo- and endoglucanases with cellotetraose is hydrolysis into cellobiose units. Accordingly, both groups of enzymes showed cellobiose as the most significant signal present. However, in some cases significant signals for glucose were detectable, showing that these enzymes are also capable of cleaving off cellotriose units directly. This effect was more significant for the endoglucanases. Exo- and endoglucanases basically showed no triose signal, indicating that in general these two groups of enzymes cannot cleave off sugar monomers.

Example 6

Synthesis of Perfluorinated Tags.

Perflurinated tags (Compound 3 and Compound 5) were obtained by coupling dimethyl-arginine (Compound 1) to perfluorinated (F17) molecules of varying length by amide bond formation (Compound 2 and Compound 4).

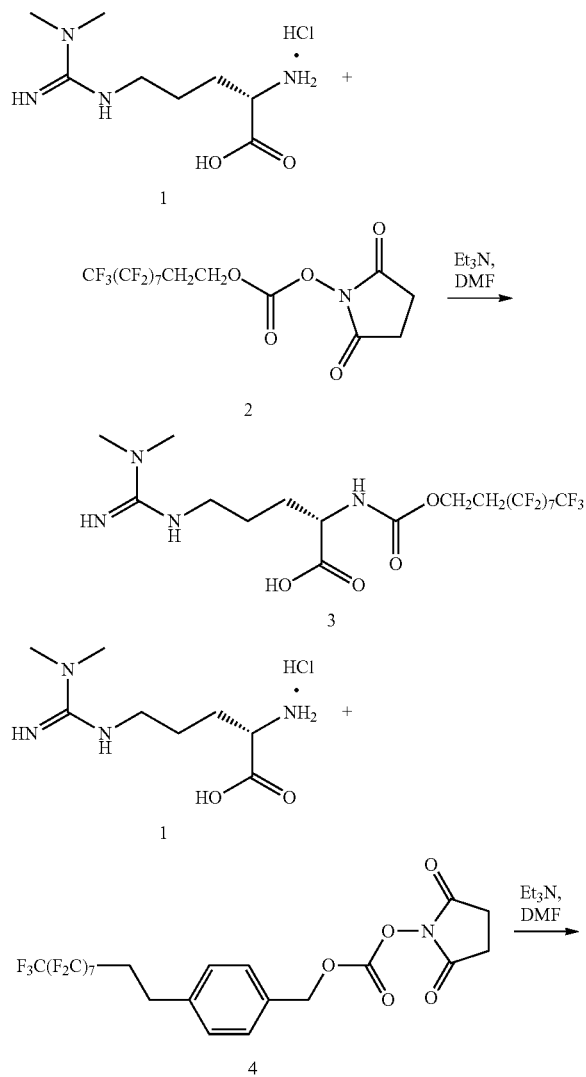

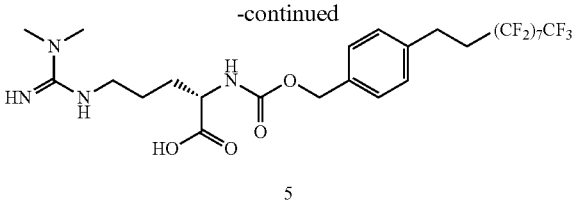

Compound 3.

Triethylamine (0.18 mL, 1.31 mmol) was added to a stirred solution of asymmetric dimethyl-arginine HCl salt (Compound 1; 120 mg, 0.436 mmol) and Compound 2 (308 mg, 0.523 mmol) in DMF (11.0 mL) under nitrogen at 0° C. Subsequently, the ice-bath was removed and the reaction mixture was stirred at room temperature overnight. The solvent was removed under reduced pressure and the residue was purified by column chromatography (MeOH/EtOAc/H$_2$O=5/3/0.1 to 5/3/1) to provide the desired Compound 3 (112 mg, 37% yield) as a white viscous solid substance. $^1$H NMR (600 MHz, CD$_3$OD) δ (ppm) 4.36 (t, J=6.0 Hz, 2H), 4.08 (t, J=7.2 Hz, 1H), 3.32-3.27 (m, 2H), 3.05 (s, 6H), 2.65-2.52 (m, 2H), 1.92-1.82 (m, 1H), 1.76-1.65 (m, 3H). LRMS (NIMS) m/z calculated for C$_{19}$H$_{21}$F$_{17}$N$_4$O$_4$, 692.13, found 692.74.

Compound 5.

Triethylamine (0.19 mL, 1.35 mmol) was added to a stirred solution of asymmetric dimethyl-arginine HCl salt (Compound 1; 125 mg, 0.450 mmol) and Compound 4 (2,5-dioxopyrrolidin-1-yl-(3,3,4,4,5,5,6,6,7,7,8,8,9,9,10,10,10-heptadecafluorodecyl)benzyl car-bonate; 380 mg, 0.550 mmol) in DMF (11.0 mL) under nitrogen at 0° C. Subsequently, the ice-bath was removed and the reaction mixture was stirred at room temperature overnight. The solvent was removed under reduced pressure and the residue was purified by column chromatography (MeOH/EtOAc/H$_2$O=5/3/0.1 to 5/3/1) to provide the desired Compound 5 (120 mg, 34% yield) as a white solid substance. $^1$H NMR (600 MHz, CD$_3$OD) δ (ppm) 7.33 (d, J=7.8 Hz, 2H), 7.27 (d, J=7.8 Hz, 2H), 5.06 (AB, J=12.6 Hz, 2H), 4.07 (t, J=6.0 Hz, 1H), 3.32-3.27 (m, 2H), 3.04 (s, 6H), 2.95-2.89 (m, 2H), 2.52-2.40 (m, 2H), 1.91-1.84 (m, 1H), 1.75-1.63 (m, 3H).

Example 7

Synthesis of xylobiose-F17. A (CH$_2$)$_5$-linker (Compound 7) was coupled to the reducing end of a xylobiose molecule (Compound 6) using Schmidt imidate chemistry to yield Compound 8. After removing the acetyl protection groups from the hydroxyl groups of the sugar molecule (Compound 9), hydrogenation by Pd/C removed the Carbobenzyloxy (Cbz) protection group to give a primary amine (Compound 10). A peptide coupling reaction with a fluorous tag (Compound 3) yielded the desired perfluorinated enzyme substrate (Compound 11).

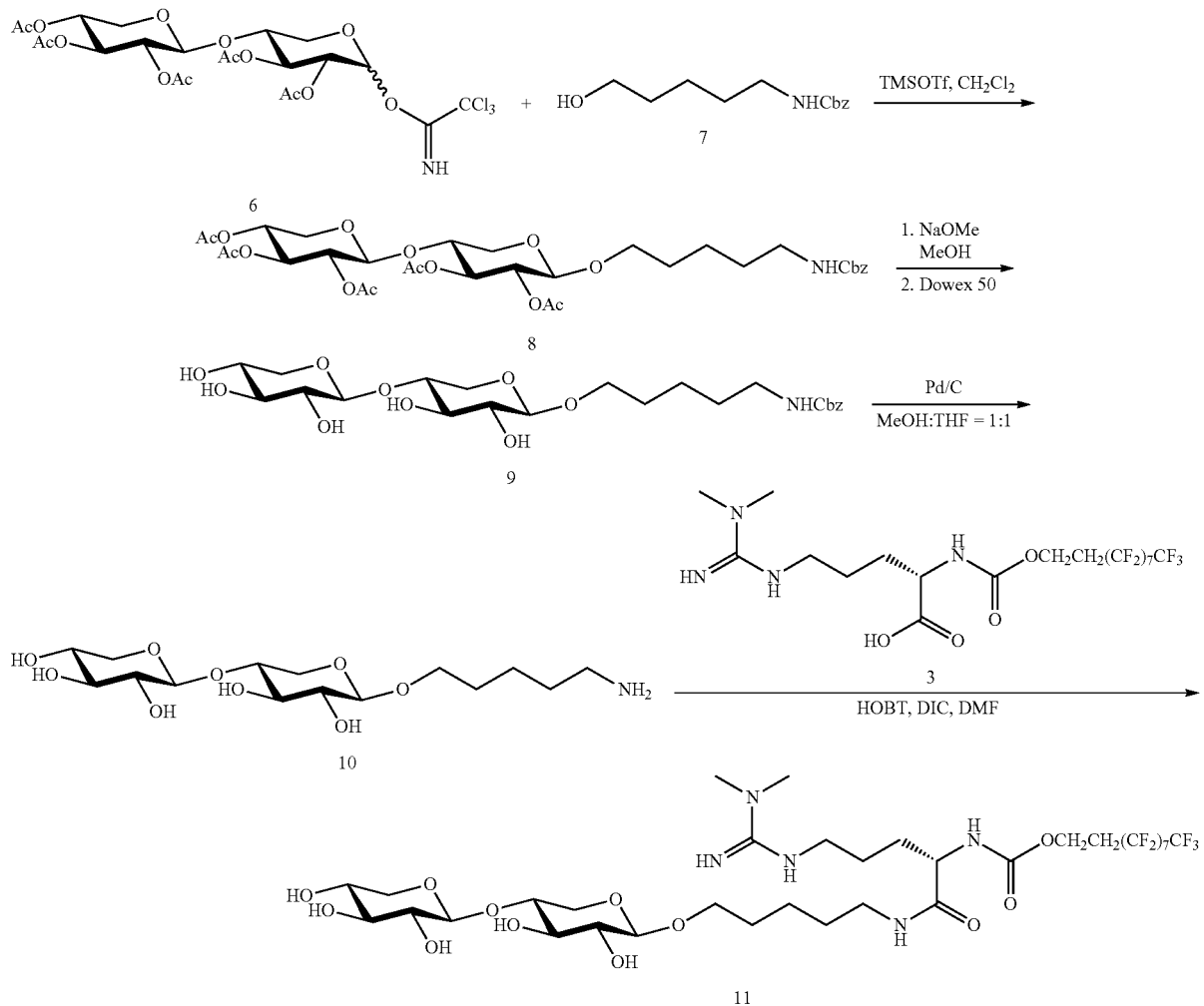

Compound 8.

Compound 6 (114 mg, 0.18 mmol), and Compound 7 (51 mg, 0.21 mmol) were mixed in 4.0 mL of anhydrous methylene chloride under nitrogen. Then 3 Å molecular sieves were added. After the resulting mixture was stirred at room temperature for 0.5 h, it was cooled to −20° C., followed by injection of TMSOTf (5 μL, 0.027 mmol). After the reaction mixture was stirred at this temperature for 1 h, triethylamine was added to quench the reaction. The solvent was removed under reduced pressure and the substance was purified by flash column chromatography to give 49 mg of Compound 8 with 37% yield. $^1$H NMR (400 MHz, CDCl$_3$) δ (ppm) 7.36-7.27 (m, 5H), 5.14-5.03 (m, 4H), 4.91-4.75 (m, 4H), 4.52 (d, J=6.0 Hz, 1H), 4.37 (d, J=7.6 Hz, 1H), 4.07 (dd, J=12.0, 4.8 Hz, 1H), 3.96 (dd, J=11.6, 5.2 Hz, 1H), 3.85-3.72 (m, 2H), 3.49-3.40 (m, 1H), 3.37 (dd, J=12.0, 7.6 Hz, 1H), 3.27 (dd, J=11.6, 10.0 Hz, 1H), 3.16 (q, J=6.8 Hz, 2H), 2.04 (s, 3H), 2.03 (s, 3H), 2.02 (s, 3H), 2.01 (s, 3H), 2.00 (s, 3H), 1.62-1.51 (m, 2H), 1.51-1.42 (m, 2H), 1.38-1.28 (m, 2H).

Compound 9.

NaOMe in MeOH (3.4 μL; 25% w/w) were added to Compound 8 (43 mg, 0.06 mmol) in 2 mL of methanol. After the resulting mixture was stirred at room temperature for 4 h, prewashed DOWEX 50WX2-200 (H+) was added. The mixture was stirred for 0.5 h and filtered. The solvent was evaporated under reduced pressure and the remaining residue was purified by flash column chromatography using 30% MeOH in chloroform to give Compound 9 (30 mg) in quantitative yield. $^1$H NMR (400 MHz, CD$_3$OD) δ (ppm) 7.40-7.28 (m, 5H), 5.07 (s, 2H), 4.31 (d, J=5.6 Hz, 1H), 4.22 (d, J=7.8 Hz, 1H), 4.01 (dd, J=11.6, 5.2 Hz, 1H), 3.91 (dd, J=11.2, 5.2 Hz, 1H), 3.82 (m, 1H), 3.64 (m, 1H), 3.58-3.48 (m, 2H), 3.45 (t, J=8.8 Hz, 1H), 3.38-3.27 (m, 2H), 3.27-3.18 (m, 3H), 3.13 (t, J=6.8 Hz, 2H), 1.67-1.59 (m, 2H), 1.58-1.48 (m, 2H), 1.47-1.36 (m, 2H).

Compound 10.

Compound 9 (163 mg, 0.325 mmol) was dissolved in a mixture of methanol (2.0 mL) and THF (2.0 mL). Then 10% Pd/C (34 mg, 0.016 mmol) was added and the reaction mixture was stirred under H2 (g; 1 atm) at room temperature for 14 h. The mixture was filtered and the filtrate was concentrated by solvent evaporization under reduced pressure. The resulting residue containing Compound 10 (117 mg, 98% yield) was used in the next step without further purification. $^1$H NMR (600 MHz, CD$_3$OD) δ (ppm) 4.32 (d, J=7.8 Hz, 1H), 4.22 (d, J=7.8 Hz, 1H), 4.00 (dd, J=11.4, 5.2 Hz, 1H), 3.91 (dd, J=11.4, 5.2 Hz, 1H), 3.82 (m, 1H), 3.64 (m, 1H), 3.58-3.48 (m, 2H), 3.45 (t, J=8.8 Hz, 1H), 3.38-3.27 (m, 2H), 3.27-3.18 (m, 3H), 3.13 (t, J=6.8 Hz, 2H), 1.67-1.59 (m, 2H), 1.58-1.48 (m, 2H), 1.47-1.36 (m, 2H).
$^{13}$C NMR (150 MHz, CD$_3$OD) (ppm) 104.85, 103.98, 78.23, 77.61, 75.93, 74.72, 74.27, 71.03, 70.54, 67.07, 64.51, 42.00, 31.85, 30.36, 24.24.

Compound 11.

N,N'-Diisopropylcarbodiimide (11 µL, 0.071 mmol) and 1-hydroxybenzotriazole (11 mg, 0.071 mmol) were added to a stirred solution of Compound 10 (26 mg, 0.071 mmol) and Compound 3 (36 mg, 0.052 mmol) in DMF (2.0 mL) at room temperature, and the reaction was kept stirring overnight. The mixture was concentrated under reduced pressure, and the residue was purified by flash column chromatography to provide Compound 11 (40 mg, 74% yield). $^1$H NMR (600 MHz, CD$_3$OD) δ (ppm) 4.43-4.34 (m, 2H), 4.32 (d, J=7.8 Hz, 1H), 4.21 (d, J=7.8 Hz, 1H), 4.11-4.05 (m, 1H), 4.02-3.96 (m, 1H), 3.89 (dd, J=10.8, 4.8 Hz, 1H), 3.87-3.74 (m, 2H), 3.65 (m, 1H), 3.66-3.59 (m, 1H), 3.58-3.46 (m, 2H), 3.46 (t, J=8.4 Hz, 1H), 3.36-3.14 (m, 7H), 3.04 (s, 6H), 2.93 (t, J=6.0 Hz, 2H), 2.69-2.53 (m, 2H), 1.85 (m, 1H), 1.78-1.60 (m, 5H), 1.60-1.47 (m, 2H), 1.47-1.36 (m, 2H).

Example 8

Synthesis of Cellobiose-F17.

A (CH$_2$)$_5$-linker (Compound 7) was coupled to the reducing end of a cellobiose molecule (Compound 12) using Schmidt imidate chemistry to yield Compound 13. After removing the acetyl protection groups from the hydroxyl groups of the sugar molecule (Compound 14), hydrogenation by Pd/C removed, the carbobenzyloxy (Cbz) protection group to give a primary amine (Compound 15). A peptide coupling reaction with a fluorous tag (Compound 3) yielded the desired perfluorinated enzyme substrate (Compound 16).

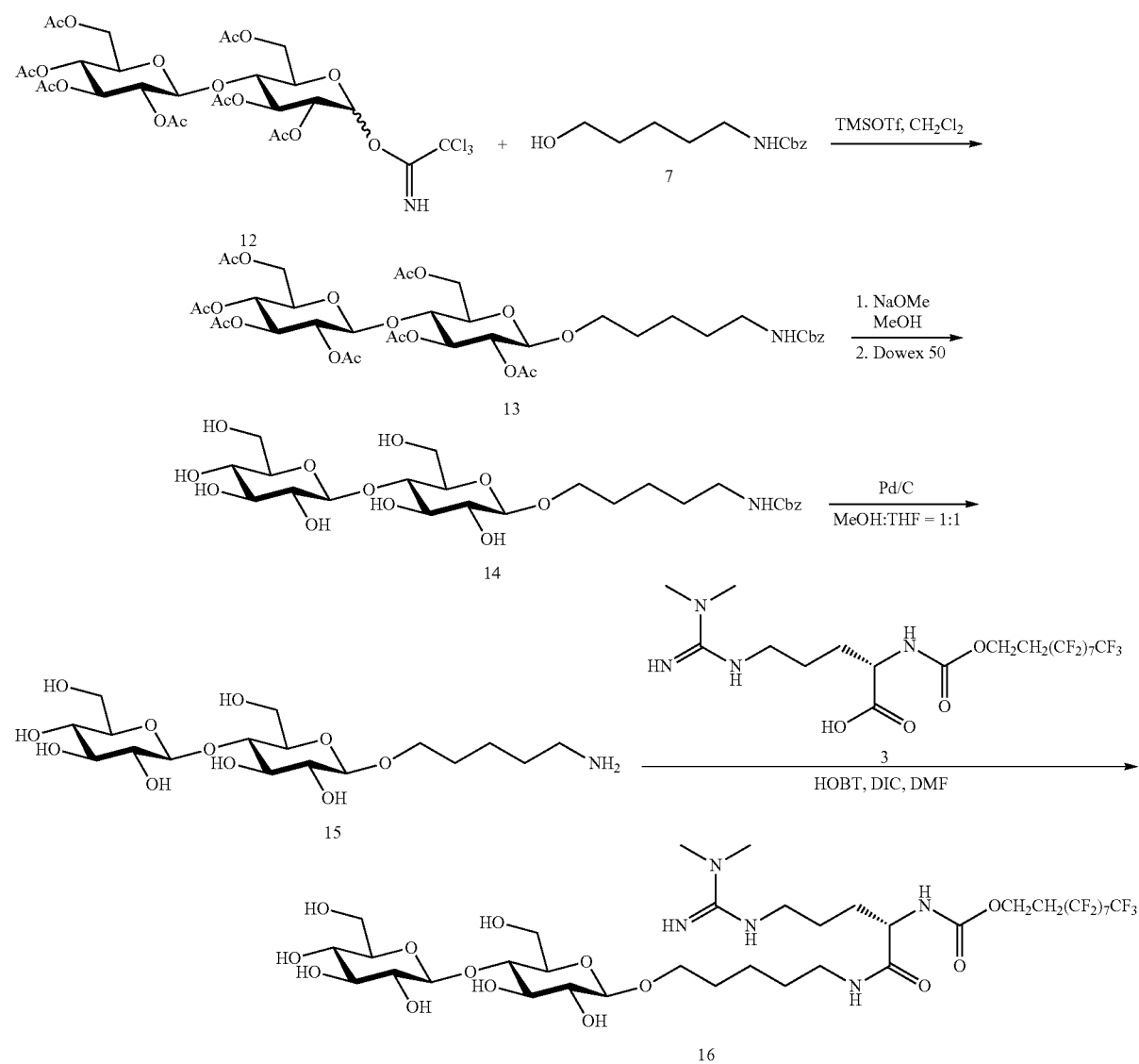

Compound 13.

Compound 12 (330 mg, 0.42 mmol) and Compound 7 (150 mg, 0.55 mmol) were mixed in 8 mL of anhydrous methylene chloride under nitrogen. Then 3 Å molecular sieves were added. After the resulting mixture was stirred at room temperature for 0.5 h, it was cooled down to −20° C., followed by injection of TMSOTf (14 µL, 0.077 mmol). After the reaction mixture was stirred at this temperature for 1 h, triethylamine was added to quench the reaction. The solvent was removed under reduced pressure and the residue was purified by flash column chromatography to give 140 mg of Compound 13 in 39% yield. $^1$H NMR (400 MHz, CDCl$_3$) δ (ppm) 7.40-7.28 (m, 5H), 5.19-5.08 (m, 5H), 4.95-4.79 (m, 3H), 4.60-4.50 (m, 2H), 4.45 (d, J=8.0 Hz, 1H), 4.39 (dd, J=12.8, 4.4 Hz, 1H), 4.18-4.00 (m, 2H), 3.88-3.75 (m, 2H), 3.69 (m, 1H), 3.61 (m, 1H), 3.48 (m, 1H), 3.20 (q, J=6.8 Hz, 2H), 2.10 (s, 3H), 2.07 (s, 3H), 2.01 (s, 3H), 2.00 (s, 6H), 1.99 (s, 3H), 1.96 (s, 3H), 1.67-1.56 (m, 2H), 1.56-1.47 (m, 2H), 1.47-1.32 (m, 2H).

Compound 14.

NaOMe in MeOH (20 μL; 25% w/w) were added to Compound 13 (217 mg, 0.25 mmol) in 2.5 mL of methanol. After the resulting mixture was stirred at room temperature for 4 h, prewashed DOWEX 50WX2-200 (H$^+$) was added. The mixture was stirred for 0.5 h and filtered. The solvent was evaporated under reduced pressure and the remaining residue was purified by flash column chromatography using 30% MeOH in chloroform to give Compound 14 (128 mg, 90% yield). $^1$H NMR (600 MHz, CD$_3$OD) δ (ppm) 7.40-7.28 (m, 5H), 5.06 (s, 2H), 4.40 (d, J=7.8 Hz, 1H), 4.27 (d, J=7.8 Hz, 1H), 3.90-3.82 (m, 4H), 3.66 (dd, J=11.4, 5.4 Hz, 1H), 3.58-3.48 (m, 3H), 3.41-3.28 (m, 4H), 3.26-3.20 (m, 2H), 3.11 (t, J=6.8 Hz, 2H), 1.67-1.58 (m, 2H), 1.55-1.46 (m, 2H), 1.45-1.35 (m, 2H).

Compound 15.

Compound 14 (89 mg, 0.16 mmol) was dissolved in a mixture of methanol (1.5 mL) and THF (1.5 mL). Then 10% Pd/C (16.8 mg, 0.008 mmol) was added and the reaction mixture was stirred under H$_2$ (g; 1 atm) at room temperature for 14 h. The mixture was filtered and the filtrate was concentrated by solvent evaporization under reduced pressure. The resulting residue containing Compound 15 (65 mg, 96% yield) was used in the next step without further purification. $^1$H NMR (600 MHz, CD$_3$OD) δ (ppm) 4.41 (d, J=7.8 Hz, 1H), 4.28 (d, J=7.8 Hz, 1H), 3.94-3.83 (m, 4H), 3.65 (dd, J=12.0, 5.4 Hz, 1H), 3.59-3.53 (m, 2H), 3.51 (t, J=9.0 Hz, 1H), 3.42-3.32 (m, 4H), 3.32-3.29 (m, 2H), 3.27-3.20 (m, 2H), 2.72 (t, J=7.2 Hz, 2H), 1.68-1.60 (m, 2H), 1.60-1.51 (m, 2H), 1.50-1.41 (m, 2H). $^{13}$C NMR (150 MHz, CD$_3$OD) δ (ppm) 104.9, 104.5, 81.1, 78.4, 78.2, 76.8, 76.7, 75.2, 75.1, 71.7, 70.9, 62.7, 62.2, 42.2, 32.2, 30.6, 24.5.

Compound 16.

N,N'-Diisopropylcarbodiimide (8.1 μL, 0.052 mmol) and 1-hydroxybenzotriazole (8.0 mg, 0.052 mmol) were added to a stirred solution of Compound 15 (22 mg, 0.052 mmol) and Compound 3 (30 mg, 0.043 mmol) in DMF (1.5 mL) at room temperature, and the reaction was kept stirring overnight. The mixture was concentrated under reduced pressure, and the residue was purified by flash column chromatography to provide Compound 16 (35 mg, 74% yield). $^1$H NMR (600 MHz, CD$_3$OD) δ (ppm) 4.41 (d, J=7.8 Hz, 1H), 4.40-4.32 (m, 2H), 4.28 (d, J=7.8 Hz, 1H), 4.10-4.04 (m, 1H), 3.94-3.83 (m, 4H), 3.66 (dd, J=12.0, 5.4 Hz, 1H), 3.61-3.47 (m, 3H), 3.44-3.25 (m, 4H), 3.25-3.16 (m, 4H), 3.04 (s, 6H), 2.96-2.91 (t, J=7.2 Hz, 2H), 2.65-2.53 (m, 2H), 1.88-1.79 (m, 1H), 1.73-1.59 (m, 5H), 1.58-1.48 (m, 2H), 1.47-1.39 (m, 2H)

Example 9

Synthesis of cellotetraose-F17. A fully acetylated cellotetraose molecule (Compound 17) was first converted to a trichloro-imidate (Compound 18), and a (CH$_2$)$_5$-linker (Compound 7) was subsequently coupled to the reducing end of the cellotetraose molecule (Compound 18) using Schmidt imidate chemistry to yield Compound 19. After removing the acetyl protection groups from the hydroxyl groups of the sugar molecule (Compound 20), hydrogenation by Pd/C removed the Carbobenzyloxy (Cbz) protection group to give a primary amine (Compound 21). A peptide coupling reaction with a fluorous tag (Compound 5) yielded the desired perfluorinated enzyme substrate (Compound 22).

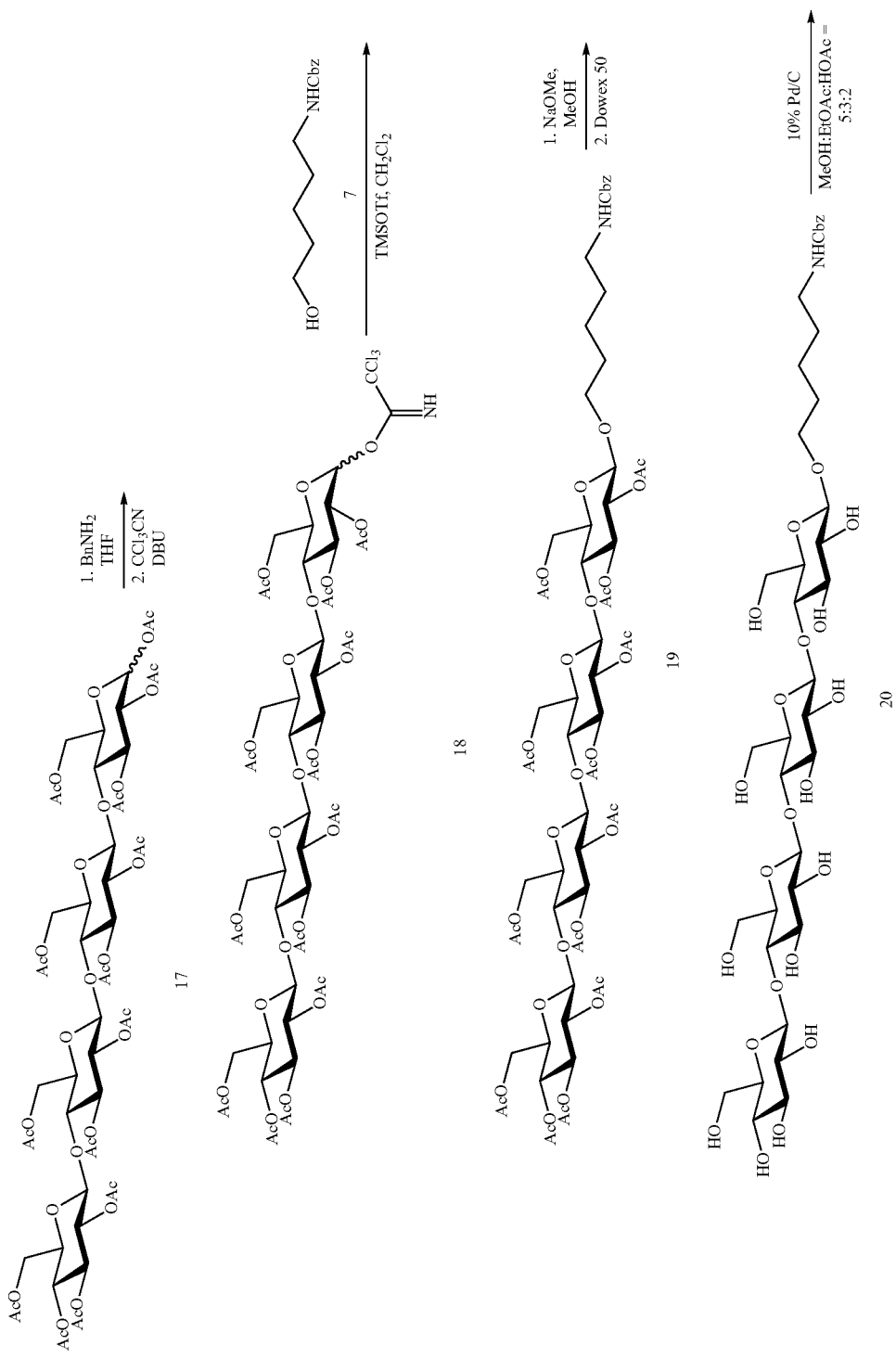

-continued
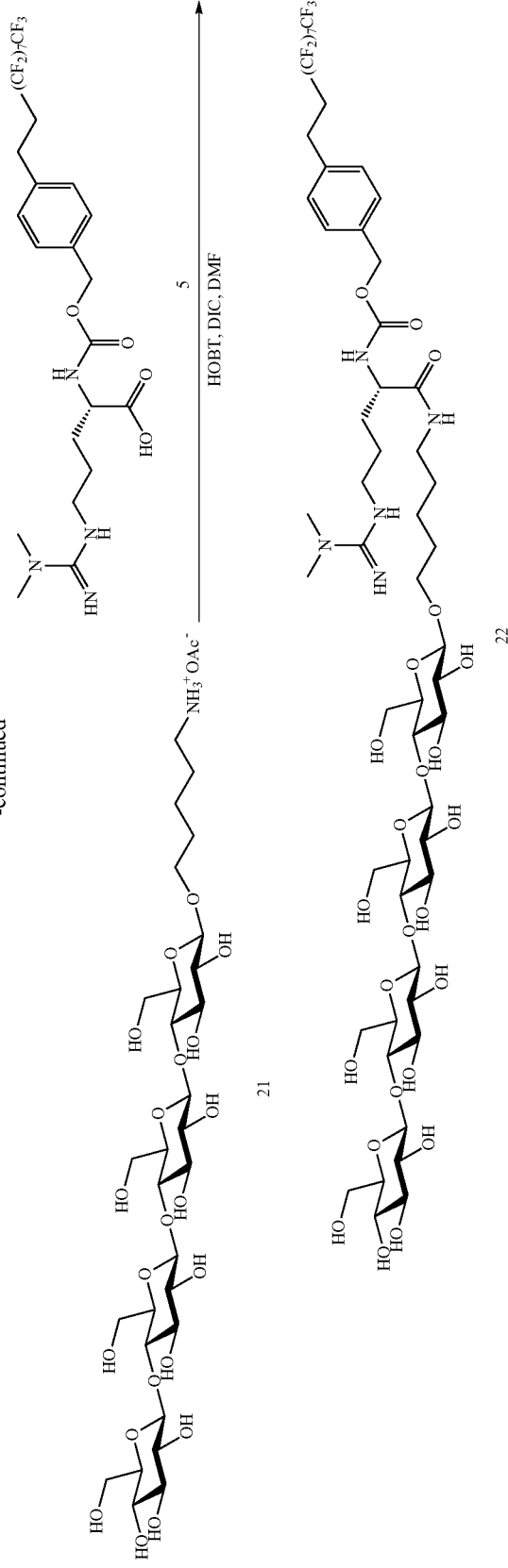

Compound 18.

Benzylamine (52 µL, 0.47 mmol) was added to a stirred solution of D-(+)-cellotetraose tetradecaacetate (Compound 17; 391 mg, 0.31 mmol) in THF (13 mL) at room temperature every 12 h for 60 h. Subsequently, the solvent was removed and the resulting residue was purified by flash column chromatography to give Compound 17 (intermediate) (365 mg, 97% yield). $CCl_3CN$ (0.30 mL, 2.97 mmol) was added to a stirred solution of Compound 17 (intermediate) (360 mg, 0.30 mmol) in methylene chloride (10.0 mL) at 0° C., followed by the addition of DBU (9 µL, 0.06 mmol). The resulting mixture was stirred for 2 h and the solvent was evaporated under reduced pressure. The residue was subjected to flash column chromatography purification to give Compound 18 (341 mg, 84% yield). $^1$H NMR (400 MHz, $CDCl_3$) δ (ppm) 8.65 (s, 1H), 6.47 (s, 1H), 5.69 (br, 1H), 5.50 (t, J=9.6 Hz, 1H), 5.16-5.00 (m, 6H), 4.90 (t, J=8.0 Hz, 1H), 4.89 (q, J=8.8 Hz, 2H), 4.55-4.38 (m, 7H), 4.34 (dd, J=12.8, 4.4 Hz, 1H), 4.15-4.05 (m, 3H), 4.34 (dd, J=12.4, 2.0 Hz, 1H), 3.85-3.68 (m, 3H), 3.66-3.51 (m, 3H), 2.14 (s, 6H), 2.11 (s, 3H), 2.08 (s, 3H), 2.034 (s, 3H), 2.031 (s, 3H), 2.02 (s, 3H), 2.01 (s, 3H), 2.00 (s, 3H), 1.998 (s, 3H), 1.99 (s, 3H), 1.98 (s, 3H), 1.96 (s, 3H).

Compound 19.

Compound 18 (112 mg, 0.0825 mmol) and Compound 7 (25 mg, 0.107 mmol) were mixed in 5 mL of anhydrous methylene chloride under nitrogen. Then 3 Å molecular sieves were added. After the resulting mixture was stirred at room temperature for 0.5 h, it was cooled down to −20° C., followed by injection of TMSOTf (14 µL, 0.077 mmol). After the reaction mixture was stirred at this temperature for 2 h, triethylamine was added to quench this reaction. The solvent was removed under reduced pressure and the residue was purified by flash column chromatography to give Compound 19 (35 mg, 30% yield). $^1$H NMR (600 MHz, $CD_3OD$) δ (ppm) 7.37-7.27 (m, 5H), 5.16-5.00 (m, 7H), 4.92-4.78 (m, 5H), 4.51 (dd, J=12.0, 1.8 Hz, 1H), 4.47-4.36 (m, 5H), 4.34 (dd, J=12.6, 4.2 Hz, 1H), 4.13-4.02 (m, 3H), 4.01 (dd, J=12.6, 2.4 Hz, 1H), 3.83-3.67 (m, 4H), 3.65-3.59 (m, 1H), 3.57-3.50 (m, 3H), 3.47-3.39 (m, 1H), 3.15 (q, J=6.8 Hz, 2H), 2.13 (s, 3H), 2.12 (s, 3H), 2.10 (s, 3H), 2.07 (s, 3H), 2.02 (s, 3H), 2.01 (s, 3H), 1.999 (s, 3H), 1.996 (s, 3H), 1.992 (s, 3H), 1.98 (s, 3H), 1.97 (s, 3H), 1.96 (s, 3H), 1.94 (s, 3H), 1.60-1.51 (m, 2H), 1.51-1.42 (m, 2H), 1.40-1.27 (m, 2H).

Compound 20.

NaOMe in MeOH (30 µL; 25% w/w) was added to Compound 19 (32 mg, 0.022 mmol) in a mixture of methanol (1.5 mL) and methylene chloride (1.5 mL). After the resulting mixture was stirred at room temperature for 14 h, prewashed DOWEX 50WX2-200 ($H^+$) was added. The mixture was stirred for 0.5 h and filtered. The solvent was evaporated under reduced pressure to give a white solid substance (18 mg; Compound 20), which was used in the next step without further purification. $^1$H NMR (600 MHz, $D_2O$) δ (ppm) 7.41-7.28 (m, 5H), 5.06 (s, 2H), 4.49 (d, J=7.8 Hz, 1H), 4.48 (d, J=7.8 Hz, 1H), 4.47 (d, J=7.8 Hz, 1H), 4.41 (d, J=7.8 Hz, 1H), 3.97-3.90 (m, 3H), 3.90-3.82 (m, 2H), 3.81-3.72 (m, 3H), 3.69 (dd, J=12.6, 6.0 Hz, 1H), 3.68-3.55 (m, 9H), 3.53 (m, 1H), 3.49-3.42 (m, 2H), 3.39-3.22 (m, 5H), 3.08 (t, J=6.0 Hz, 2H), 1.61-1.53 (m, 2H), 1.50-1.43 (m, 2H), 1.35-1.28 (m, 2H).

Compound 21.

Compound 20 (18 mg, 0.020 mmol) was dissolved in a mixture of methanol (1.5 mL), ethyl acetate (1.5 mL), and acetic acid (1.0 mL). Then 10% Pd/C (18 mg, 0.008 mmol) was added and the reaction mixture was stirred under $H_2$ (g; 1 atm) at room temperature for 14 hours. The mixture was filtered and the filtrate was concentrated by solvent evaporation under reduced pressure. The resulting residue (14 mg; Compound 21) was used in the next step without further purification. $^1$H NMR (600 MHz, $D_2O$) δ (ppm) 4.51-4.47 (m, 2H), 4.46 (d, J=7.8 Hz, 1H), 4.43 (d, J=8.4 Hz, 1H), 3.94-3.81 (m, 5H), 3.80-3.71 (m, 3H), 3.70-3.49 (m, 9H), 3.48-3.39 (m, 2H), 3.40-3.33 (m, 1H), 3.31 (t, J=8.4 Hz, 2H), 3.28-3.21 (m, 2H), 2.95 (t, J=7.2 Hz, 2H), 1.67-1.56 (m, 4H), 1.43-1.35 (m, 2H).

Compound 22.

N,N'-Diisopropylcarbodiimide (1.0 µL, 0.0063 mmol) and 1-hydroxybenzo-triazole (1.0 mg, 0.0063 mmol) were added to a stirred solution of Compound 21 (4.0 mg, 0.0053 mmol) and Compound 5 (4.1 mg, 0.0053 mmol) in DMF (0.4 mL) at room temperature, and the reaction was kept stirring overnight. The resulting mixture containing Compound 22 was purified by flash column chromatography as before, however, in this case it was not possible to purify sufficiently enough for NMR. Nanostructure-initiator mass spectrometry was used to confirm the success of the coupling reaction. The calculated exact mass for $C_{55}H_{78}F_{17}N_5O_{24}$ is 1515.48, which was correctly identified at 1516.45 $[M+H]^+$ (Figure S8).

Example 10

Figure 9:
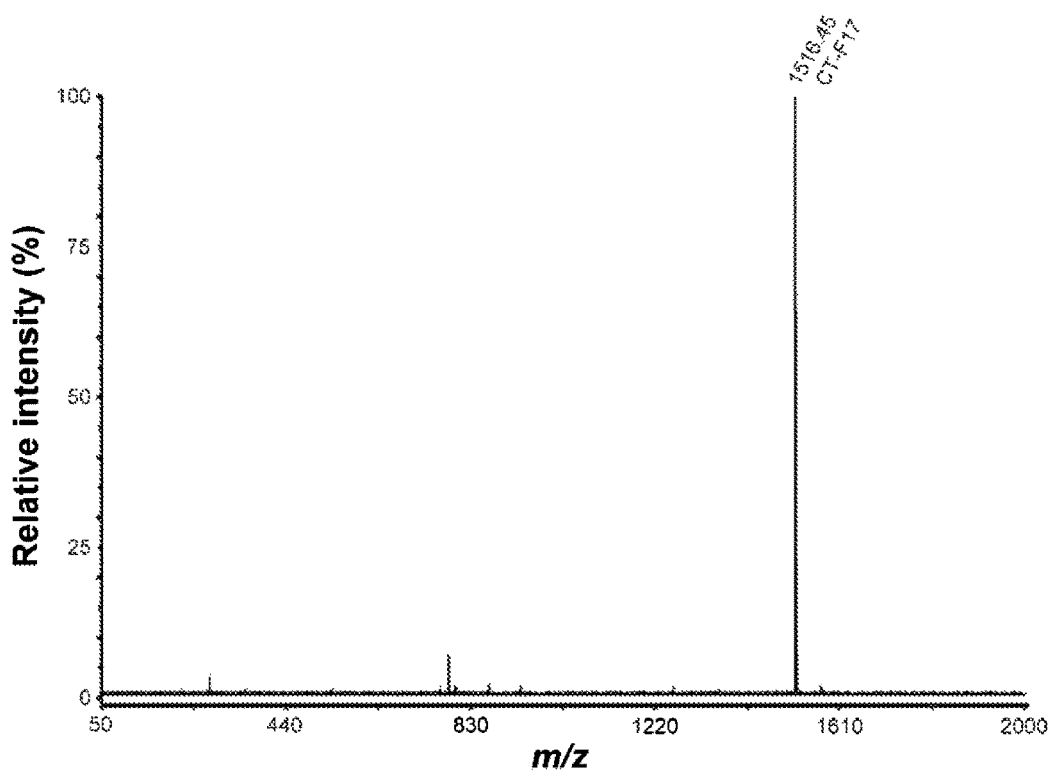
FIG. 9 is a mass spectrum of cellotetraose-F17.

Mass spectrum of cellotetraose-F17 (FIG. 9). After synthesis, cellotetraose-F17 (CT-F17) was purified by flash column chromatography. Purity was controlled by nanostructure-initiator mass spectrometry.

Example 11

Figure 10:
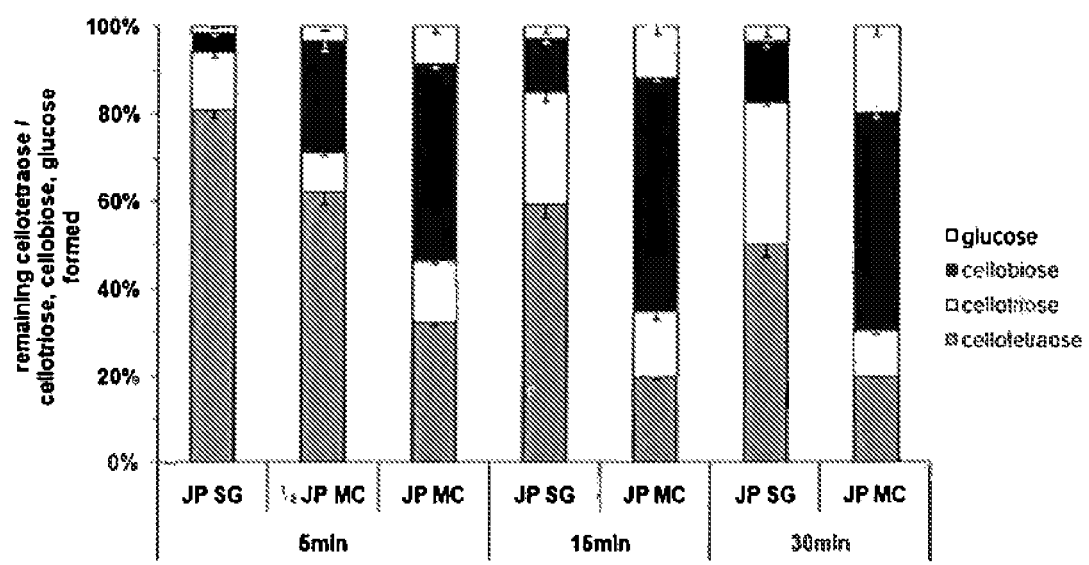
FIG. 10 is a bar graph showing the influence of a carbon source on enzyme expression.

The influence of carbon source on enzyme expression was determined (FIG. 10). A Jepson Prairie environmental sample (JP) was incubated in minimal medium containing either switchgrass (SG) or microcrystalline cellulose (MC) as sole carbon source. The resulting secretomes were used for glycohydrolase activity assays using perfluorinated cellotetraose as substrate. Conversion of cellotetraose into smaller sugar chains was monitored over time with sampling time points after 5 min, 15 min, and 30 min. At 5 min an additional JP MC sample with only half the amount of secretome was included.

Example 12

Nanostructure-Initiator Mass Spectrometry (NIMS)

Fabrication of NIMS chips. A 4" silicon wafer (single-sided polished P/Boron, orientation <1-0-0>, resistivity 0.01-0.02 Ωcm, thickness 525±25 µm) obtained from Silicon Quest International (Santa Clara, Calif.) was cut into a 70×70 mm square and cleaned thoroughly with methanol, followed by anodic etching with 25% hydrofluoric acid in ethanol in a custom made Teflon etching chamber using extreme caution. A current of 2.4 A was applied for 15 minutes. After etching, chips were coated by adding 400 µL of the initiator liquid bis(heptadecafluoro-1,1,2,2-tetrahydrodecyl)tetramethyl-disiloxane (Gelest; Morrisville, Pa.) for 20 minutes. Excess initiator was blown off with nitrogen.

Mass Spectrometry.

In each case 0.5-1 µL per quenched reaction sample was spotted onto the NIMS surface and removed after an incubation of ~30 s. A grid drawn manually on the NIMS chip using a diamond-tip scribe helped with spotting and identification of sample spots in the spectrometer. Chips were loaded using a modified standard MALDI plate. NIMS was

Example 13

Detection of Lipase Activity 2 ul lipase substrate F17008-Gly-Cys(palmitoyl)-Met-Gly-Leu-Pro-Art-OH was mixed with a lipase sample (2 ul solution of purified Lipase from *Candida rugosa* (Sigma, St. Louis) at 0.06 units/ul) in 5 ul phosphate buffer (pH7.5) in a microwell plate.

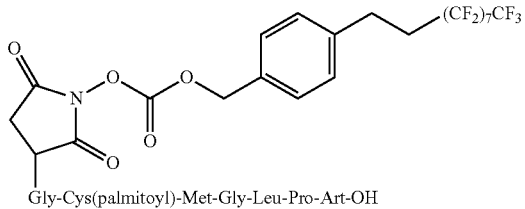

Gly-Cys(palmitoyl)-Met-Gly-Leu-Pro-Art-OH

Lipase Substrate F17008-Gly-Cys(palmitoyl)-Met-Gly-Leu-Pro-Art-OH

Figure 11A:
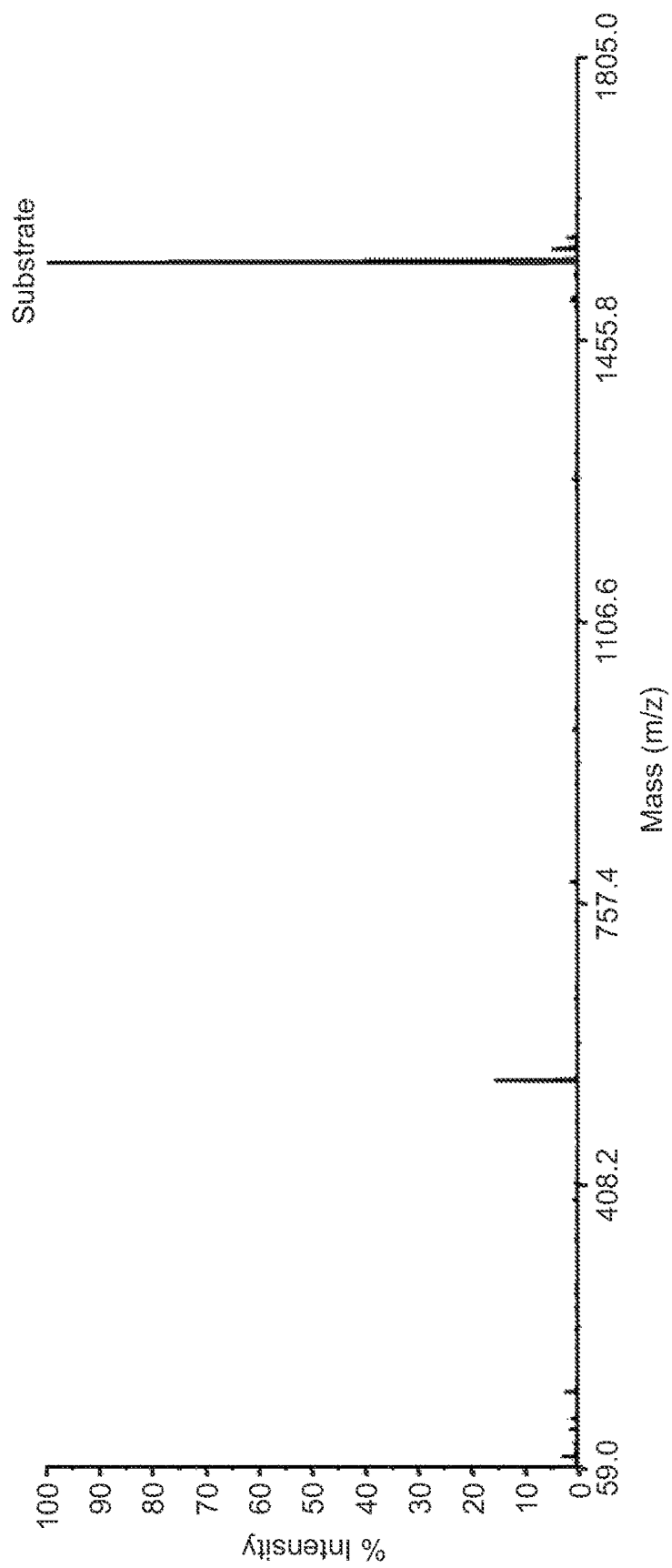
FIGS. 11a and 11b are mass spectra showing signals for lipase substrate F17008-Gly-Cys(palmitoyl)-Met-Gly-Leu-Pro-Art-OH and product F17008-Gly-Cys-Met-Gly-Leu-Pro-Art-OH.
Figure 11B:
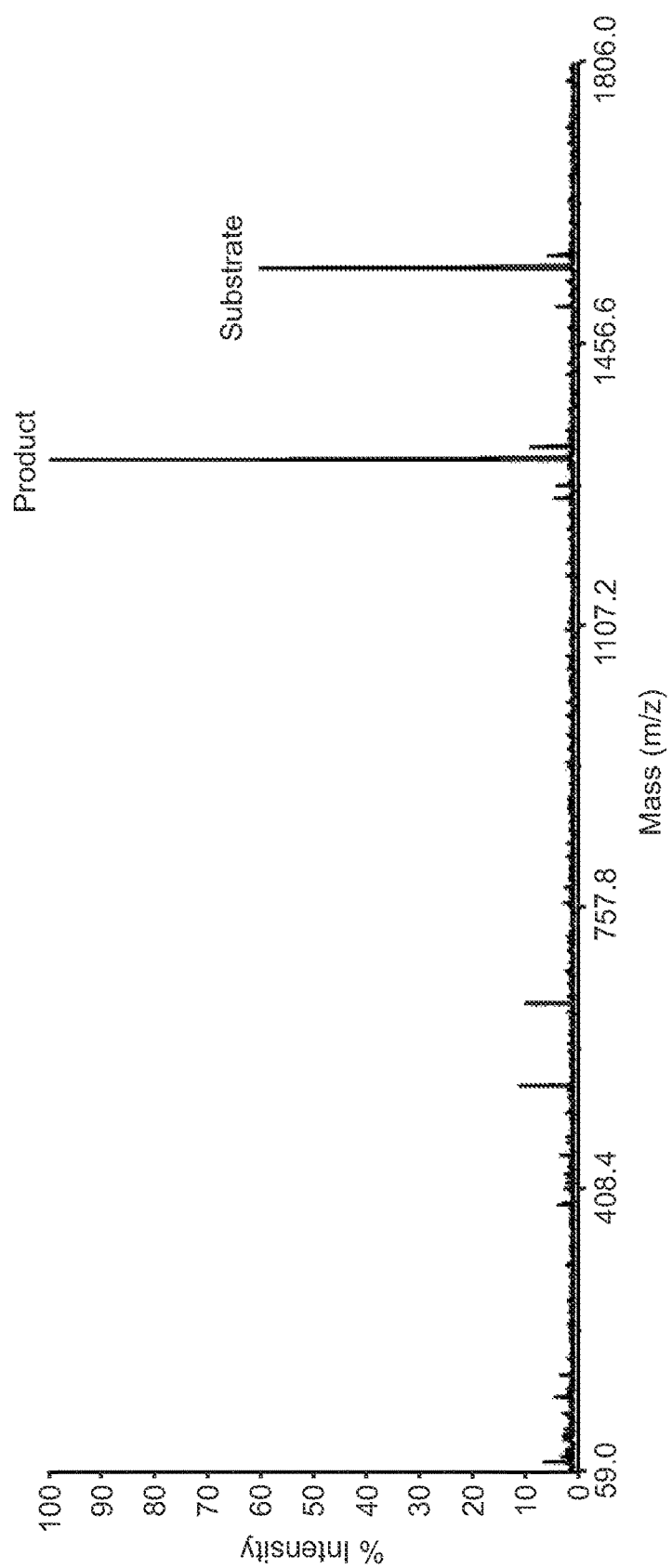

The mixture was incubated for 15 minutes at 37° C. and reaction were quenched by adding 3 ul of ice-cold methanol (analytical grade) and kept on ice for NIMS-based analysis. The resulting mass spectra from the NIMS-analysis are shown in FIG. 11*a-b*. FIG. 11*a* shows the signals for lipase substrate F17008-Gly-Cys(palmitoyl)-Met-Gly-Leu-Pro-Art-OH and FIG. 11*b* shows the signals for the lipase substrate and the reaction product F17008-Gly-Cys-Met-Gly-Leu-Pro-Art-OH.

This example demonstrates that the method disclosed herein can be used for analysis of lipase activity in a sample.

Example 14

Detection of Protease Activity 2 ul protease substrate F17008-Ala-Pro-Ay-Thr-Pro-Gly-Gly-Arg-Arg-OH was mixed with a protease sample (2 ul solution of purified trypsin (Sigma, St. Louis) at 0.08 units/ul) in 5 ul phosphate buffer (pH7.5) in a microwell plate.

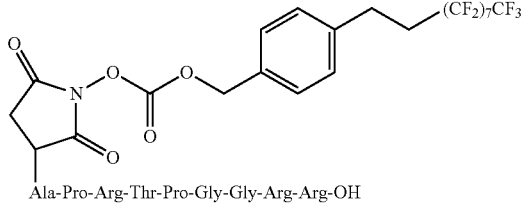

Ala-Pro-Arg-Thr-Pro-Gly-Gly-Arg-Arg-OH

Protease Substrate F17008-Ala-Pro-Ay-Thr-Pro-Gly-Gly-Arg-Arg-OH

Figure 12A:
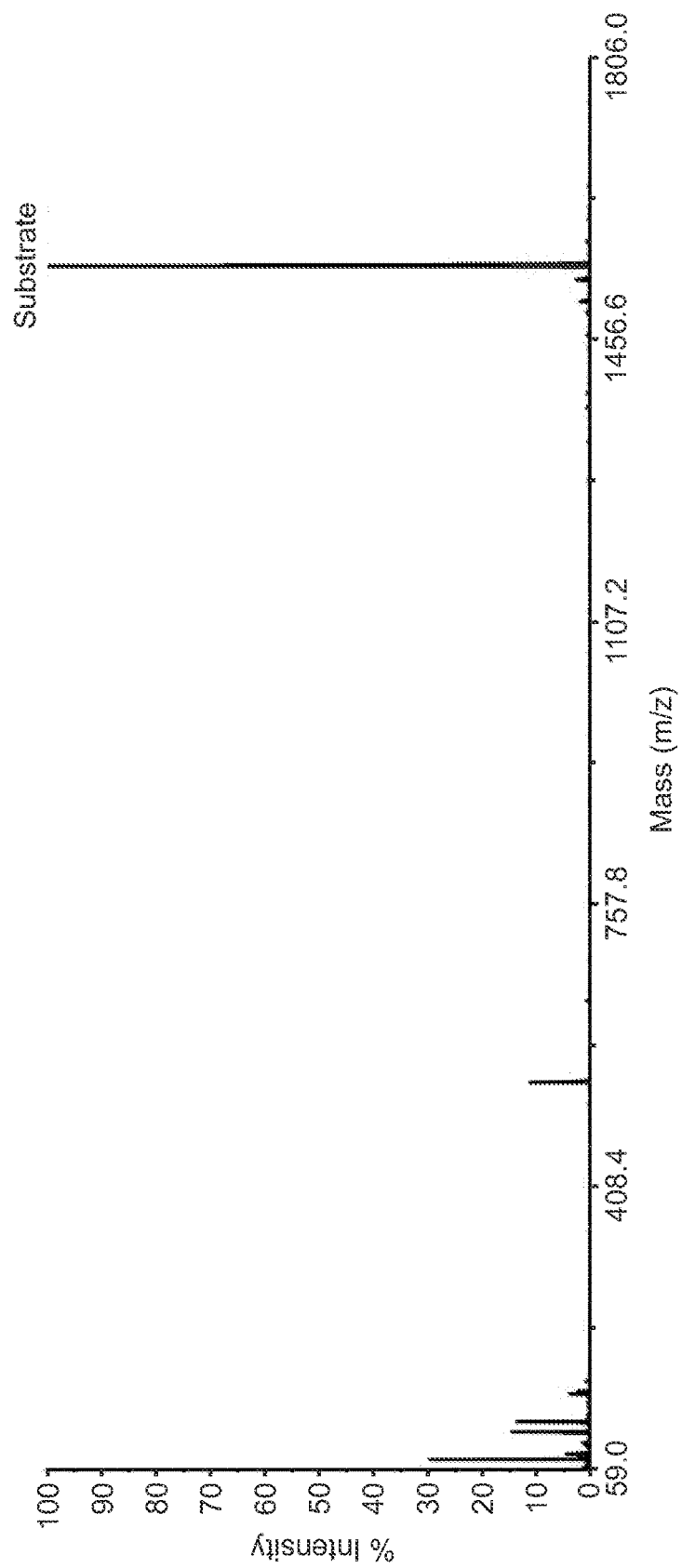
FIGS. 12a and 12b are mass spectra showing signals for protease substrate F17008-Ala-Pro-Arg-Thr-Pro-Gly-Gly-Arg-Arg-OH and product F17008-Ala-Pro.
Figure 12B:
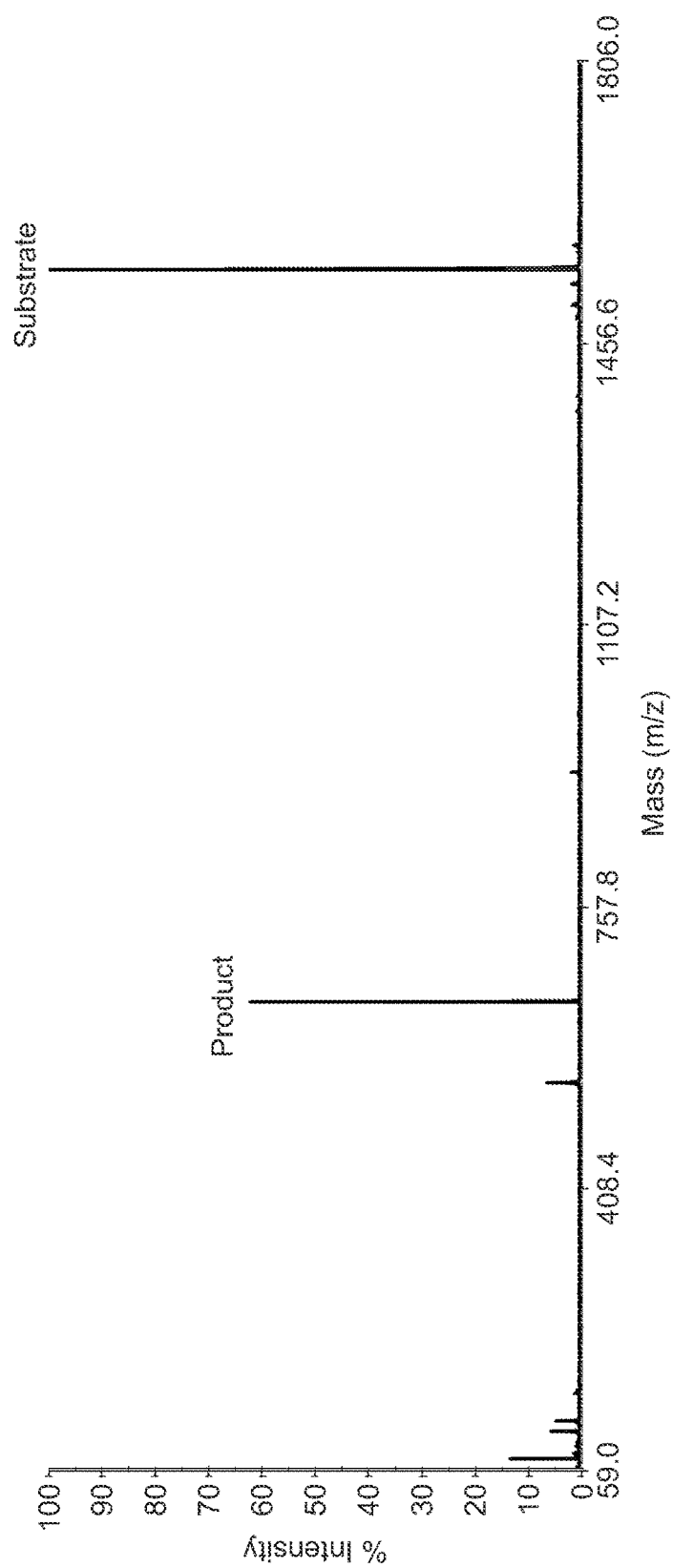

The mixture was incubated for 15 minutes at 37° C. and reaction were quenched by adding 3 ul of ice-cold methanol (analytical grade) and kept on ice for NIMS-based analysis. The resulting mass spectra from the NEVIS-analysis are shown in FIG. 12*a-b*. FIG. 12*a* shows the signals for protease substrate F17008-Ala-Pro-Ay-Thr-Pro-Gly-Gly-Arg-Arg-OH and FIG. 12*b* shows the signals for the protease substrate and the reaction product F17008-Ala-Pro.

This example demonstrates that the method disclosed herein can be used for analysis of protease activity in a sample.

What is claimed is:

1. A method of detecting the activities of a plurality of enzymes in a multiplexed assay, comprising:
    (a) providing an aqueous solution comprising substrates for a plurality of enzymes, wherein each of the substrates comprises a substrate head group linked to a hydrophobic fluorous tag and forms micelles in the aqueous solution, wherein the substrate head group is selected from the group consisting of a sugar head group, a lipid head group, and a polypeptide head group;
    (b) incubating the aqueous solution comprising the substrates with a sample comprising the plurality of enzymes to carry out enzymatic reactions to form reaction products under aqueous conditions in a container, wherein the plurality of enzymes comprises enzymes having an activity that changes the mass of said substrates;
    (c) applying the reaction products formed in (b) to a hydrophobic nanostructure-initiator mass spectrometry (NIMS) chip surface after incubating the sample with the aqueous solution comprising the substrates, wherein the hydrophobic NIMS chip surface comprises a perfluorinated coating configured to interact with the hydrophobic fluorous tags of the substrates;
    (d) analyzing the reaction products and the substrates by mass spectrometry; and
    (e) detecting a change in the mass of the substrate to identify the ratio of substrate-to-reaction product ions in a mass spectrum, wherein a change in the mass of the substrate is indicative of an activity of one or more of the plurality of enzymes in the sample.

2. The method of claim 1, wherein the plurality of enzymes comprises an enzyme with plant cell wall degrading activity.

3. The method of claim 2, wherein the enzyme with plant cell wall degrading activity reduces the chain length of a sugar head group.

4. The method of claim 3, wherein the sugar comprises cellulose or hemicellulose.

5. The method of claim 2, wherein the enzyme is a cellulase or a hemicellulase.

6. The method of claim 2, wherein the enzyme with plant cell wall degrading activity degrades lignin.

7. The method of claim 6, wherein the enzyme with plant cell wall degrading activity is a laccase.

8. The method of claim 1, wherein the sample comprises isolated enzymes or is a crude environmental sample.

9. The method of claim 1, wherein the sample is obtained by incubating a crude environmental sample with switchgrass or cellulose.

10. The method of claim 1, wherein two or more of the reaction products are analyzed in parallel and wherein two or more of the reaction products are different in mass.

11. The method of claim 10, wherein the reaction products comprise sugar molecules with identical mass and tags of different mass.

12. The method of claim 10, wherein the reaction products comprise sugar molecules of different mass and tags of identical mass.

13. The method of claim 1, wherein the plurality of enzymes comprises a hydrolase.

14. The method of claim 13, wherein the hydrolase is a glucoside hydrolase.

15. The method of claim 1, wherein the container is a tube or a microwell plate.

16. The method of claim 1, further comprising quenching the enzymatic reactions before applying the reaction products to the hydrophobic NIMS chip surface.

17. The method of claim 1, wherein the perfluorinated coating of the NIMS chip surface comprises bis(heptadecafluoro-1,1,2,2-tetrahydrodecyl)tetramethyl-disiloxane.

18. The method of claim 1, wherein the plurality of enzymes comprises a lipase.

19. The method of claim 1, wherein the plurality of enzymes comprises a protease.

20. The method of claim 1, wherein the hydrophobic fluorous tag is a perfluorinated heptadecafluoro-1,1,2,2-tetrahydrodecyl (F17) tag, or bis(tridecafluoro-1,1,2,2-tetrahydrooctyldimethylsiloxy)-methylchloro-silane (F26) tag.

* * * * *